(12) United States Patent
Mercolino

(10) Patent No.: US 7,874,489 B2
(45) Date of Patent: Jan. 25, 2011

(54) PRODUCT AUTHENTICATION

(75) Inventor: Thomas J. Mercolino, Stockton, NJ (US)

(73) Assignee: AuthentiForm Technologies, LLC, Chapel Hill, NC (US)

(*) Notice: Subject to any disclaimer, the term of this patent is extended or adjusted under 35 U.S.C. 154(b) by 760 days.

(21) Appl. No.: 11/455,817

(22) Filed: Jun. 20, 2006

(65) Prior Publication Data

US 2007/0012784 A1    Jan. 18, 2007

Related U.S. Application Data

(60) Provisional application No. 60/692,225, filed on Jun. 20, 2005.

(51) Int. Cl.
*G06K 19/06* (2006.01)

(52) U.S. Cl. ..................... 235/491; 235/494

(58) Field of Classification Search .......... 235/494, 235/487, 380, 491
See application file for complete search history.

(56) References Cited

U.S. PATENT DOCUMENTS

| | | | |
|---|---|---|---|
| 4,250,382 A | 2/1981 | Libby | |
| 4,345,604 A | 8/1982 | Renirie | |
| 4,423,819 A | 1/1984 | Cummings | |
| 5,139,812 A | 8/1992 | Lebacq | |
| 5,451,505 A | 9/1995 | Dollinger | |
| 6,458,595 B1 | 10/2002 | Selinfreund | |
| 6,522,945 B2 | 2/2003 | Sleep et al. | |
| 6,714,299 B2 | 3/2004 | Peterson et al. | |
| 6,799,725 B1 | 10/2004 | Hess et al. | |
| 6,869,015 B2 | 3/2005 | Cummings et al. | |
| 6,892,178 B1 | 5/2005 | Zacharia | |
| 6,948,068 B2 | 9/2005 | Lawandy et al. | |
| 6,968,231 B1 | 11/2005 | Silvian et al. | |
| 7,052,737 B2 | 5/2006 | Kool et al. | |
| 7,256,398 B2 | 8/2007 | Ross et al. | |
| 7,378,675 B2 | 5/2008 | Ross et al. | |
| 7,392,950 B2 | 7/2008 | Walmsley et al. | |
| 7,507,588 B2 | 3/2009 | Mehrpouyan et al. | |
| 7,720,254 B2 | 5/2010 | Stierman et al. | |
| 7,752,137 B2 | 7/2010 | Dillon | |

(Continued)

FOREIGN PATENT DOCUMENTS

EP    0650546 B1    10/1997

(Continued)

OTHER PUBLICATIONS

Golub, T.R., et al., Molecular Classification of Cancer: Class Discovery and Class Prediction by Gene Expression Monitoring, Science, Oct. 15, 1999, pp. 531-537, vol. 286, www.sciencemag.org.

(Continued)

*Primary Examiner*—Karl D. Frech
(74) *Attorney, Agent, or Firm*—Deborah H. Spencer; Moore & Van Allen PLLC

(57) ABSTRACT

The present invention provides methods, reagents, and apparatus for authenticating products. Methods of the invention are easy to implement but difficult to replicate, simulate, alter, transpose, or tamper with. In particular, the present invention relates to a product authentication code defined by a signature array of a population of entities, and its use thereof.

31 Claims, 9 Drawing Sheets

U.S. PATENT DOCUMENTS

| | | | |
|---|---|---|---|
| 2001/0037455 A1 | 11/2001 | Lawandy et al. | |
| 2002/0048822 A1 | 4/2002 | Rittenburg et al. | |
| 2002/0066543 A1 | 6/2002 | Lilly | |
| 2002/0129251 A1 | 9/2002 | Itakura et al. | |
| 2003/0141375 A1 | 7/2003 | Lawandy | |
| 2004/0061702 A1 | 4/2004 | Kincaid | |
| 2004/0126840 A1 | 7/2004 | Cheng et al. | |
| 2004/0166063 A1 | 8/2004 | Siegel | |
| 2004/0185481 A1 | 9/2004 | Numajiri | |
| 2005/0031838 A1 | 2/2005 | Lagunowich et al. | |
| 2005/0060171 A1 | 3/2005 | Molnar | |
| 2005/0100204 A1 | 5/2005 | Afzal et al. | |
| 2005/0108044 A1 | 5/2005 | Koster | |
| 2005/0112610 A1 | 5/2005 | Lee et al. | |
| 2006/0119913 A1 | 6/2006 | Moon | |
| 2006/0131517 A1 | 6/2006 | Ross et al. | |
| 2006/0249588 A1* | 11/2006 | Walmsley et al. | 235/494 |
| 2007/0012783 A1 | 1/2007 | Mercolino | |
| 2007/0172429 A1 | 7/2007 | Gao et al. | |
| 2008/0034426 A1 | 2/2008 | Stierman et al. | |
| 2009/0084859 A1* | 4/2009 | Lapstun et al. | 235/494 |
| 2010/0128925 A1 | 5/2010 | Stierman et al. | |

FOREIGN PATENT DOCUMENTS

| | | |
|---|---|---|
| EP | 1998710 | 12/2008 |
| EP | 1999873 | 12/2008 |
| EP | 2011008 | 1/2009 |
| GB | 2220346 | 10/1990 |
| WO | 0151915 A1 | 7/2001 |
| WO | 03039648 A2 | 5/2003 |
| WO | 2004038645 A1 | 5/2004 |
| WO | 2007002009 A2 | 1/2007 |
| WO | 2007002016 A2 | 1/2007 |
| WO | 2007021971 A2 | 2/2007 |
| WO | 2007106512 A2 | 9/2007 |
| WO | 2007106514 A3 | 9/2007 |
| WO | 2007106515 A3 | 9/2007 |
| WO | 2007149127 A1 | 12/2007 |

OTHER PUBLICATIONS

Zhi, Z., et al., Multianalyte immunoassay with self-assembled addressable microparticle array on a chip, Analytical Biochemistry, 2003, pp. 236-243, vol. 318, Elsevier Science.

Wolfrum, C., et al., Oligonucleotides as Coding Molecules in an Anti-Counterfeiting System, Nucleosides, Nucleotides, and Nucleic Acids, 2005, pp. 1069-1074, vol. 24 (5-7).

Co-pending U.S. Appl. No. 11/455,817 dated Jun. 20, 2006.

Patent Cooperation Treaty, International Preliminary Report on Patentability, Dec. 22, 2008, PCT/US2006/062374.

Patent Cooperation Treaty, Written Opinion of the International Search Authority, Jul. 31, 2007, PCT/US2006/062374.

Patent Cooperation Treaty, International Preliminary Report on Patentability, Mar. 17, 2009, PCT/US2006/023876.

Patent Cooperation Treaty, Written Opinion of the International Search Authority, Apr. 16, 2008, PCT/US2006/023876.

Patent Cooperation Treaty, International Preliminary Report on Patentability, Dec. 24, 2007, PCT/US2006/023868.

Patent Cooperation Treaty, Written Opinion of the International Search Authority, Apr. 25, 2007, PCT/US2006/023868.

Hobby Industry Technology Site, Manufacturers Guide to Bar Code Common Forms and EC/EDI, May 2001, pp. 1-4.

* cited by examiner

PRODUCT AUTHENTICATION

CROSS-REFERENCE TO RELATED APPLICATIONS

This patent application claims priority from U.S. Provisional Patent Application No. 60/692,225 filed Jun. 20, 2005 entitled "Product Identification", the contents of which are hereby incorporated herein in their entirety.

FIELD OF THE INVENTION

This invention is in the general field of methods, reagents, and apparatus for authenticating products. In particular, the invention relates to a product authentication code defined by a signature array of a population of entities, and its uses thereof.

BACKGROUND OF THE INVENTION

Product counterfeiting is a major worldwide problem experienced in connection with many different products. It is estimated that 5% of all world trade in branded goods is counterfeit (ten Ham, *Drug Saf.*, 2003, 26: 991-7). A counterfeit product often appears confusingly similar to that of a genuine product. The material of a counterfeit product may be the same as, or different from the material of a genuine product. Often the counterfeiting product has inferior quality as compared to that of a genuine product.

Drug counterfeiting has become a significant issue in the healthcare community and the pharmaceutical industry worldwide. A report published in the open-access health journal PloS Medicine suggests that up to 15 percent of all drugs sold worldwide—worth of $35 billion (€25bn)—are counterfeit. Drug counterfeiting threatens to impose great health risks to customers who buy the counterfeit drug in the expectation that they are buying a genuine drug. Because of the absence of safety regulations compared to authentic equivalents, counterfeit drugs often have substandard drug quality, quantity, or harmful ingredients. In addition, as a result of counterfeiting, legitimate pharmaceutical companies can lose significant revenues. It can be difficult to distinguish a counterfeit drug having a chemical formulation similar to that of a genuine drug, but made by substandard manufacturing procedures. Likewise, it can also be difficult to distinguish a counterfeit product produced by diluting the genuine product. A report released by the Centre for Medicines in the Public Interest, in the United States, projects counterfeit drug sales to reach US$ 75 billion in 2010, a 92% increase from 2005.

Methods have been developed to identify genuine products and distinguish them from counterfeit products. For example, various analytical methods have been used to detect components in pharmaceutical products, with emphasis on the identification of differences among manufacturers that can be used for source verification in suspect/counterfeit cases. Such methods include, but are not limited to, capillary electrophoresis (Flurer et al, *Journal of Chromatography, A,* 1994, 674: 153-63), thin-layer chromatography (Pachaly et al., *Pharmazeutische Industrie,* 1993, 55: 259-67), near-infrared spectroscopy (Scafi et al, *Analyst.* 2001, 126: 2218-24; and Olsen et al., *Pharmaceutical Technology North America,* 2002, 26: 62-71), and calorimetric assay (Green et al, *Tropical Medicine & International Health,* 2001, 6: 980-982).

Other methods have been developed to establish identity and source of the product, sometimes including a pharmaceutical product, by marking the product. For example, bar code symbols placed on the outside of the medication may be used for prescription medication identification (U.S. Pat. No. 5,845,264); a mixture of at least two photochromic compounds that have different absorption maxima in the activated state may be incorporated into a carrier composition, e.g., ink, paint, fiber or polymer to form the authenticating display data on the article (U.S. Pat. No. 5,289,547); a solution of a target nucleic acid may be incorporated in an object for security crypto-marking of the object (U.S. Pat. No. 5,139,812); a hapten may be associated with the product as a marker (U.S. Pat. No. 5,429,952); compositions that are uniquely luminescent may be incorporated or applied to materials for verifying products or documents (U.S. Pat. No. 6,402,986); and constituents intrinsically located or extrinsically placed in an object (such as a pharmaceutical) may be detected by x-ray fluorescence analysis to identify or verify the object or its point of manufacture (US 20040022355). In addition, U.S. Pat. No. 5,599,578 describes a method for labeling an object for its verification by applying a mark to said object with a visible ink that contains a component that is invisible to the naked eye, such as a dye that is visible only in the presence of selected radiation, or an ink that displays a selected measurable electrical resistivity, or an ink containing a biologic marker. WO 2004041328 describes methods for marking a pharmaceutical product, container or pharmaceutical packaging system with a scent to establish the identity and/or source of the pharmaceutical.

The substance(s) used to mark a product can be visible, such as a dye or colored molecule. They can also be invisible to the unaided eyes, thus are a "covert" marker of a substance. Covert markers are typically more difficult to replicate, simulate, alter, transpose, and are less subject to tampering. WO 2005111127 describes a method for incorporating covert markers into an article in the form of metals and their salts and oxides into plastics, then detecting net changes in magnetic field around said article.

Microparticles have been used to mark a product for authentication. In some embodiments, microparticles have been used as the "cargo" to host the coding elements like molecules or nanoparticles with identifiable features (Finkel et al., Oct. 1, 2004, *Analytical Chemistry,* 352A-359A, and references therein). U.S. Pat. No. 4,053,433 describes a method of marking a substance with microparticles that are encoded with an orderly sequence of visually distinguishable colored segments that can be decoded with a microscope or other magnifying device. Additionally, microparticles have been used as part of the coding element, where the physical properties of the microparticles are used as the coding elements, and most code deciphering is accomplished by recognizing a physical pattern formed by the compilation of various microparticles (Finkel et al., 2004 supra and references therein). U.S. Pat. No. 4,767,205 discloses an identification method involving an identification code that is based upon a selected number of groups of microparticles, wherein each group is made of highly uniform microparticles of substantially the same uniform size, shape and color with the specific combination of size, shape and color in one group not being repeated in any other group. U.S. Pat. No. 6,647,649 discloses a process for marking an article by applying thereto a tag, which comprises a plurality of microparticles having two or more distinguishable marker layers corresponding to a predetermined numeric code.

Despite these efforts, drug counterfeiting remains a worldwide problem. There is a continuing need to develop novel methods to combat counterfeit drugs at the manufacturing stage and for detection in the distribution chain. One effective way to fight counterfeiting is to mark a product with an authentication or product identification code that is not easily imitated or counterfeited. The present invention provides such a product authentication code and describes its uses.

SUMMARY OF THE INVENTION

The present invention provides methods, reagents, and apparatus for authenticating products. Methods of the invention are easy to implement and can be covert, but are difficult to replicate, simulate, alter, or transpose, and resist tampering and inadvertent or intentional alteration.

In one general aspect, the invention provides a method of marking a product for product authentication, comprising the steps of: a) associating a population of entities with the product, wherein the population comprises at least two distinct clusters of entities having detectable counts or relative counts of entities per cluster; and b) assigning a signature array of the population of entities to the product as a product authentication code, wherein the signature array comprises information about the counts or relative counts of entities of at least two distinct clusters of entities within the population.

Another general aspect of the invention is a coded product comprising a product and a product authentication code wherein the product authentication code is encoded by a signature array of a population of entities associated with the product, wherein the signature array comprises information about the counts or relative counts of entities of at least two distinct clusters of entities within the population.

Another general aspect of the invention is an improvement to a product, wherein the improvement is a product authentication code that is encoded by a signature array of a population of entities associated with the product, wherein the signature array comprises information about the counts or relative counts of entities of at least two distinct clusters of entities within the population.

The invention also provides a method of determining a signature array of a population of entities, comprising the steps of: a) classifying entities within the population into at least two distinct clusters of entities; b) determining the counts or relative counts of entities within each of the at least two distinct clusters of entities; and c) combining the information about the counts or relative counts of entities of the at least two distinct clusters of entities into an array.

One other general aspect of the present invention is a method of authenticating a product, comprising the steps of: a) associating a population of entities with the product, wherein the population comprises at least two distinct clusters of entities having detectable counts or relative counts of entities per cluster; b) assigning a signature array of the population of entities to the product as a product authentication code, wherein the signature array comprises information about the counts or relative counts of entities of at least two distinct clusters of entities within the population; wherein information about the signature array and the product authentication code is recorded; c) analyzing the product to obtain a measured signature array of the population of entities associated with the product; d) comparing the measured signature array with that which is expected based on the recorded information; and e) accepting the product as authenticate when the measured signature array matches that which is expected.

Another general aspect of the invention is a method for quality control and release of products from a manufacturing process, comprising the steps of: a) associating a population of entities with a product during the manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) analyzing the product to obtain a measured signature array of the population of entities associated with the product; c) comparing the measured signature array with that which is expected based on the recorded information; and d) releasing products manufactured by the manufacturing process when the measured signature array matches that which is expected.

In a particular embodiment of the invention, the population of entities comprises a combination or plurality of microparticles. In another particular embodiment, the population of entities comprises a combination or plurality of printed symbols.

In preferred embodiments of the invention, the product is a pharmaceutical product.

DETAILED DESCRIPTION OF THE INVENTION

Figure 1:
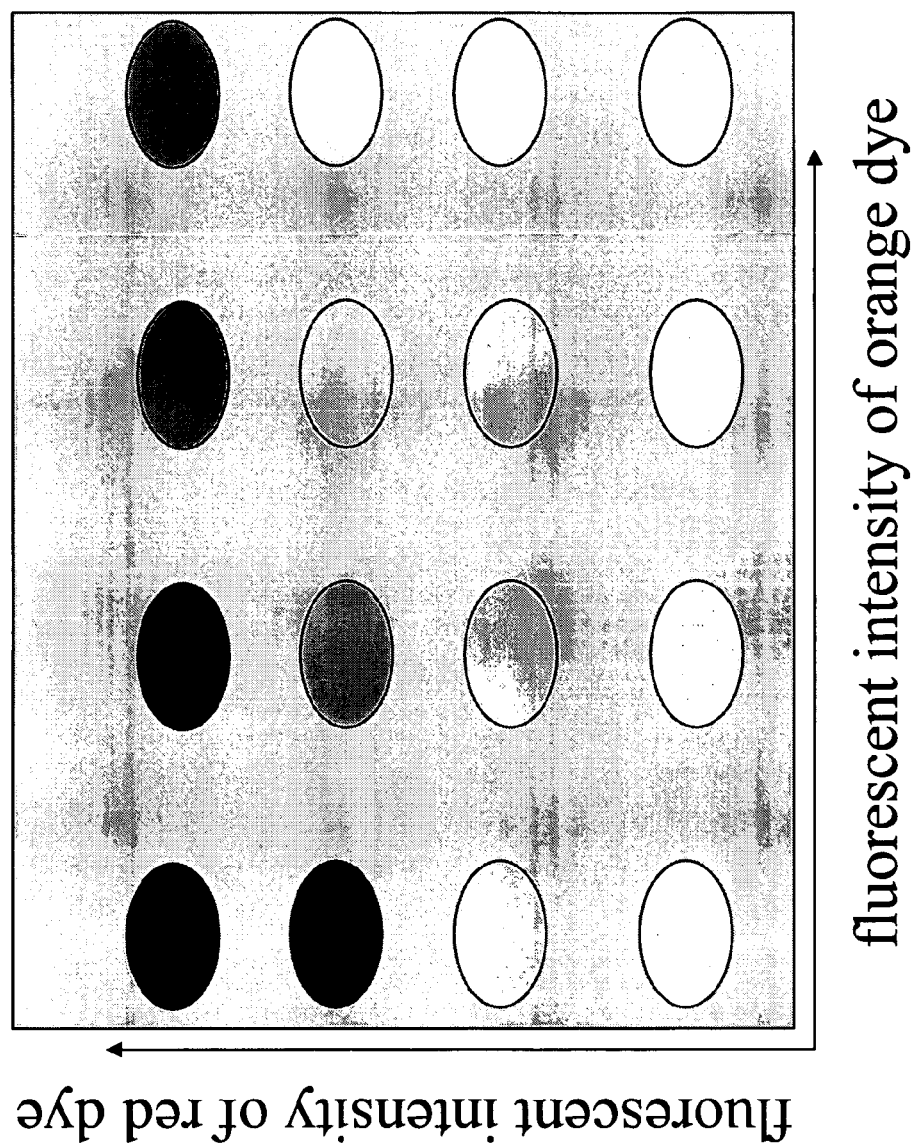
FIG. 1 illustrates the classification into clusters of a population of heterogeneous microparticles labeled with different intensities of two fluorescent dyes, red and orange. X-axis represents fluorescent intensity of orange dye and Y-axis represents fluorescent intensity of the red dye.

All publications cited below are hereby incorporated by reference. Unless defined otherwise, all technical and scientific terms used herein will have the commonly understood meaning to one of ordinary skill in the art to which this invention pertains.

It must be noted that as used herein and in the appended claims, the singular forms "a," "an," and "the" include plural reference unless the context clearly dictates otherwise. Thus, for example, a reference to "a population of entities" is a reference to one or more populations of entities and includes equivalents thereof known to those skilled in the art and so forth.

As used herein, the term "array" means a collection of data items arranged in such a way so that each data item in the array can be located.

As used herein, a "cluster of entities" or a "cluster" means a classification of at least two entities that are grouped together because they share one or more discretely measurable common properties. In particular embodiments of the invention, the entities within "a cluster of entities" share one, two, three, four, five, six, seven, eight, nine, ten, or more discretely measurable common properties.

As used herein, the "count of entities per cluster", the "number of entities per cluster", the "count (or number) of entities within a cluster", and the "count (or number) of entities of a cluster" are used interchangeably to mean the number or sum total of entities within a cluster. The "count of entities per cluster" can be obtained by counting discrete entities within the cluster by means such as an automated counter or manual counting method.

As used herein, the term "counterfeit" when applied as a description to a product or drug means a product made in imitation of a genuine product or drug with intent to deceive. As used herein, the terms "counterfeit drug" and "counterfeit pharmaceutical product" may be used interchangeably. For example, a counterfeit drug is a composition that has not received approval by a governmental authority (e.g., the Food and Drug Administration of the United States) to be safe and efficacious for medical purpose in human subjects, but is labeled as a genuine pharmaceutical product. Another example of a counterfeit drug is a pharmaceutical composition that has been tampered, such as by dilution. A "counterfeit drug" also includes a composition that contains the same active ingredient(s) as that of a genuine pharmaceutical product, but is made by a party who is not legally entitled to do so, and that party passes off the composition as that of a genuine pharmaceutical product. A "counterfeit drug" as used herein also includes drug diversion or "grey market drug". Drug diversion occurs when a counterfeiter acquires genuine, non-counterfeit drugs that are targeted for one market and sells them in a different market for a profit. The counterfeiter does this to circumvent the manufacturer's goal of controlling the supply of the drugs in a particular market. As a consequence, the counterfeiter benefits from the sales in that limited supply market or in the diverted sales market.

As used herein, the term "data item" or "datum" means a single member of data.

As used herein, the term "data" means two or more individual facts or pieces of information.

As used herein, a "discretely measurable common property" is a property of or associated with each individual entity within a single cluster, and said property can be measured from the individual entity. The discretely measurable common property allows an entity to be assigned into a particular cluster. Entities having the same set of one or more discretely measurable common properties can be assigned into the same cluster. Entities having different sets of discretely measurable common properties can be assigned into distinct clusters.

Examples of "discretely measurable common property" include, but are not limited to, the properties of one or more tags associated with entities of a cluster, such as the fluorescent intensity or spectra when the entity is labeled with a fluorescent tag, the sizes of the entities, the shape of the entities, and other properties of the entities, such as being magnetic or not, density, or solid characterization, or the nucleotide sequence or amino acid sequence when the entities are composed of nucleic acid molecules or peptides/polypeptides.

As used herein, "distinct clusters of entities" means clusters that are different because entities within one cluster having at least one discretely measurable common property that is not shared with the entities within the other cluster(s). Thus clusters of entities can be distinguished from one and another by the measurement of any of the discretely measurable common properties shared by entities within one cluster but not by entities within the other cluster(s)—the distinct discretely measurable common properties. For example, the clusters of entities can be distinguished by sizes, density or solidity including elasticity, brittle fracture, water-content etc. The particle size can be measured, for example, in a flow cytometry apparatus by so-called forward or small-angle scatter light or by microscopic examination. The clusters of entities can also be distinguished by shape. The shape of the particle can be discriminated, for example, by flow cytometry, by high-resolution slit-scanning method or by microscopic examination. The shape of a printed dot, for example, can be measured by a scanner. The clusters of entities can further be distinguished by tags, such as by fluorescent dyes with different emission wavelengths. Even when they are labeled with the same tag(s), the clusters of entities can still be distinguished because of different concentrations, intensity, or amounts of the tag associated with the entities, or the different ratios of tags on individual entities. Clusters of entities can be distinguished even when all entities share one or more discretely measurable common properties (e.g., particle size and particle shape), but do not share at least one other discretely measurable common property (e.g., intensity or amount of fluorescent tag per entity). Methods known to a person skilled in the art can be used to measure the quality or quantity of tags. In addition, the clusters of entities can be differentiated by other property or characteristic of the entities, such as being magnetic or not. When the entities are composed of or labeled with nucleic acid or peptide molecules, the clusters of entities can be differentiated by their sequences.

It is understood by a person skilled in the art that there is a basic distinction between measurement and counting. The result of counting, for example, the count of entities within a cluster, is exact because it involves discrete entities that are not subdivided into fractions. The result of measurement, on the other hand, involves measurement units that may be subdivided into smaller and smaller fractions and is thus always an estimate. A good measurement should be both accurate and precise. Accuracy is determined by the care taken by the person making the measurement and the condition of the instrument; a worn or broken instrument or one carelessly used may give an inaccurate result. Precision, on the other hand, is determined by the design of the instrument; the finer the graduations on the instrument's scale and the greater the ease with which they can be read, the more precise the measurement. The choice of the instrument used should be appropriate to the desired precision of the results. A person skilled in the art knows how to choose an appropriate instrument for a particular measurement.

In order to detect the count or relative count of entities within distinct clusters of a population, the clusters of entities must first be distinguished based on the measurement of the distinct discretely measurable common property or properties. It is readily apparent to a skilled artisan that the detection of the count or relative count of entities within distinct clusters of a population thus depends on the accuracy and precision of the measurement of the distinct discretely measurable common property or properties. If the distinct discretely measurable common property can not be reproducibly measured, the clusters can not be distinguished with confidence, thus the count or relative count of entities within distinct clusters can not be detected. Therefore, a condition precedent to detecting count or relative count of entities within distinct clusters of a population is the reproducible measurement of the distinct discretely measurable common property. In the present invention, at least two distinct clusters of entities are mixed in a population wherein the clusters are distinguishable by one or more distinct discretely measurable common properties that can be reproducibly measured. Thus, the counts or relative counts of entities within the distinct clusters of the population of the present invention are detectable.

As used herein, the terms "drug" and "pharmaceutical product" may be used interchangeably. The terms mean a composition that has received approval by a governmental authority (e.g., the Food and Drug Administration of the United States) to be safe and efficacious for medical purpose in human subjects. The "drug" can be in any physical state, such as being solid, liquid, or semi-liquid. The "drug" can be in any form of formulation, such as being an oral, topical, injectable, or parental pharmaceutical product.

As used herein, the term "entity" means a thing or composition that can exist separately or independently from other things. Examples of entities that can be used in the present invention include, but are not limited to, microparticles, printed symbols, nucleic acid molecules, or peptides/polypeptides.

As used herein, the terms "microparticle", "microsphere", "microbead", "bead", "microsphere", and "particle" are used interchangeably and bear equivalent meanings with respect to their particulate nature, understanding that particles can have various shapes and sizes. Preferred particles range in size from approximately 10 nm to about 200 µm in diameter or width and height in the case of nonspherical particles. For example, the particles can have a size of 0.05-50 µm, 0.1-20 µm, 1-20 µm, or 3-10 µm in diameter. The microparticles can have a different shape, such as a sphere, cube, rod or pyramid.

Those of ordinary skill in the art can use microspheres of various compositions. For example, styrene monomers polymerized into hard rigid latex spheres have been used as calibration aids at high magnifications. These latex spheres are known for their high level of inertness in the electron beam, and clusters constructed from groups of such particles within non-overlapping size ranges of approximately 0.05 to 2 microns may be detected by electron microscopy or light-scattering investigations. Likewise, the particles can be made of many other types of materials. For example, the microparticles can be made of polystyrene or latex material. Other types of acceptable polymeric microspheres include, but are not limited to, brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, POLYOX, EUDRAGIT, sugar spheres, hydrofuran, PLGA (poly(lactic coglycolic acid)) or combinations thereof. In general, such particles can be made by a copolymerization process wherein monomers, e.g., unsaturated aldehydes or acrylates, are allowed to polymerize in the presence of one or more tags, e.g., fluorescein isothiocynate (FITC), in the reaction mixture (see for example U.S. Pat. No. 4,267,234 issued to Rembaum; U.S. Pat. No. 4,267,235 Rembaum et al; U.S. Pat. No. 4,552,812, Margel et al.; U.S. Pat. No. 4,677,138, Margel). The microparticles can be produced, for example, by extrusion or spherenization.

In another embodiment, the entities can be printed symbols. As used herein, the term "printed symbol" means any symbol that is placed on or otherwise applied to a surface of a material. The "printed symbol" can be in any form or shape. For example, it can be dots, letters, or other visible or invisible signs. The "printed symbol" can have different shapes, such as square, circle, triangle, diamond, or any other shapes that can be distinctively measured. The "printed symbol" can also have different fonts or sizes. For example, the printed symbols can have a size of 0.05-1 µm, 1-20 µm, 50-100 µm, or 0.1-5 mm in diameter, width, or length in the cases where the printed symbols are not round in shape. The "printed symbol" can be any printable characters selected among many alternative identities, for example, symbols or Greek alphabet characters, the Roman alphabet characters, or any other letters of any language. Further, the font size and or style of the "printed symbol" could be replaced with any number of alternatives, for example, font color, italics, striking-through, highlighting or the like. Whole words or logos may replace individual characters to be used as "printed symbols". The "printed symbol" can also be any symbols, including those designated as symbols in the word-processing program MICROSOFT WORD.

The "printed symbol" can be placed on or applied to the surface of a material by a variety of means. For example, it can be applied to a printable surface by printing; or it can be applied to a surface by dropping, spraying, painting, rolling coating, embossing, debossing, etc.

Additionally, microprinting is an alternative to the conventional printing used in this example. Microprinting is an anti-counterfeiting technique used most often on currency and bank checks, as well as various other items of value. Microprinting involves printing very small text, usually too small to read with the naked eye, onto the note or item. Microprint is frequently hidden in an inconspicuous, unnoticeable area on the note or item, but may be placed in a prominent location on the item, and may even be labeled with an "MP" symbol as a warning that the note or item contains microprinting. For example, U.S. Pat. No. 6,214,766 relates generally to a method for producing security paper which involves printing microdot images using a colorless ink containing starch, such dots to be revealed by exposure to iodine.

To increase the per volume information content, the entity can be labeled with one or more tags that are visible or invisible to naked eyes. The term "tag" or "taggant" as used herein can be any composition that is suitable for the purpose of detecting or identification. The tag can be overt, covert, or invisible or otherwise difficult to detect on individual entities or small numbers of entities, yet having an overt signal detectable from all or a larger number of entities. For example, the entity can be labeled with one or more colors, fluorescent dyes, ultraviolet radiation dyes, luminescent compositions, hapten, nucleotides, polypeptides, or scents. A single entity can be labeled with more than one tag of the same or different types. For example, a particle can be labeled with two or more discretely distinguishable dyes in varying proportion; or a particle can be labeled with a nucleotide and a fluorescent dye. Any of the known tags and the combinations of the tags with entities can be used in the invention. Methods known to those skilled in the art can be used to label an entity with one or more tag. For example, U.S. Pat. No. 6,632,526 teaches methods of dyeing or staining microspheres with at least two fluorescent dyes in such a manner that intra-sample variation of dye concentrations are substantially minimized. The entity can be a segmented particle whose composition is varied along the diameter or the length of the particle. U.S. Pat. No. 6,919,009 teaches methods of manufacture of rod-shaped particles.

In one particular embodiment, the entity can be an entity that is labeled with or affixed to other entities. For example, the entity can be a symbol printed with an ink containing microparticles. Another example of an entity, according to this embodiment, is a particle that is covalently or non-covalently affixed with one or more other particles. US 20060054506 describes submicron-sized particles or labels that can be covalently or non-covalently affixed to entities of interest for the purpose of quantification, location, identification, tracking, and diagnosis.

The entity that can be used in the present invention preferably can be ingestible and/or non-toxic in amounts used. For example, the entity can be a liposome microparticle, i.e., a particle formed by a lipid bilayer enclosing an aqueous compartment. The entity can also be a microparticle made of pulverized cellulose material, see for example the abstract of JP0 6,298,650. The entity can further be microparticles made of calcium, such as milk calcium, inorganic calcium or organic calcium. For example, edible oil-containing calcium microparticles can be obtained following the teaching of U.S. Pat. No. 6,159,504. Biodegradable polymers, such as dextran and polylactic acid, can also be used to prepare ingestible microparticles. In addition, the edible microparticles include solid lipophilic microparticles comprising a lipophilic substance, hyaluronic acid or an inorganic salt thereof. Exemplary lipophilic particles are disclosed in US 20030064105.

The entity can be magnetic. U.S. Pat. No. 6,773,812 describes hybrid microspheres constructed using fluorescent or luminescent microspheres and magnetic nanoparticles. Distinct clusters of microspheres can be constructed based on fluorescent intensities by analogy to the clusters described in Example 1 infra, and separations can be affected based on the variable degree of magnetic content to aid in the analysis of the cluster membership on devices like the Immunicon CELLSEARCH instrument. The various microspheres disclosed in U.S. Pat. No. 6,773,812 can be used in the present invention. The particles can also have any other property that facilitates collection, separation, or identification of the particles.

The entity can also be made of chemically inert materials to enhance the survival of the entity in a chemical or biological environment, including materials resistant to heat, high or low pH, etc. The entity can further be made of materials that are non-toxic, or materials that can serve as carriers for the active ingredient. The entity can even be made from the active ingredient of a pharmaceutical product.

As used herein, a "population of entities" or a "population" means a collection of a combination or plurality of entities that include two or more distinct clusters of entities, wherein entities within one cluster have one or more discretely measurable common properties that are different from that of entities within another cluster from the same population.

As used herein, the term "relative counts of entities per cluster" means a ratio of the count of entities per cluster relative to another number. In some embodiments, the other number is the count of entities within a different cluster. In other embodiments, the other number is the total count of entities within two or more clusters of a population of entities. In other embodiments, the other number is representative of the amount or concentration of the cluster or the population of entities, such as unit volume or weight of the cluster or the population of entities. In yet other embodiments, the other number is representative of the amount or concentration of a product the cluster is associated with, or the amount or concentration of a portion or a component of the product.

As used herein, the term "a representative number of entities within a population of entities" refers to a fraction or a portion of the population of entities which contains the same clusters of entities and the same count of entities per unit of each cluster as those of the population.

For illustrative purpose, in one specific embodiment of the invention, the population of entities is composed of microparticles each simultaneously labeled with two or more fluorescent dyes, for example, according to U.S. Pat. No. 6,632,526 or U.S. Pat. No. 6,649,414. The microparticles can also be purchased from a commercial source, such as Luminex Corporation (Austin, Tex.). For example, the particles can be labeled with two dyes, such as a red fluorescent dye, 1,3-bis[(1,3-dihydro-1,3,3-trimethyl-2H-indol-2-ylidene)methyl]-2,4-dihydroxy-cyclobutenediylium, bis(inner salt) (Dye 1) and an orange fluorescent dye, 2-(3,5-dimethylpyrrol-2-yl)-4-(3,5-dimethyl-2H-pyrrol-2-ylidene)-3-hydroxy-2-cyclobuten-1-one (Dye 2). As is readily appreciated, other combinations of dyes with other colors and other chemical compositions can also be used to label microparticles. One skilled in the art can select among a variety of suitable dyes such as, for example, the dyes recited in U.S. Pat. No. 6,649,414, depending upon desired emission/absorption and hydrophobic properties, etc. Where fluorescent dyes are used, the dyes are chosen such that the emission maxima of the dyes used preferably falls about in the center of the fluorescence detection channels of the measurement device used. Preferably the dyes used have emission maxima separated by greater than 10 nm, 25 nm, or 50 nm from each other.

Microparticles within the population are heterogeneous because they do not share at least one distinctly measurable property (e.g., intensity or amount of fluorescent tag per entity). The fluorescent intensity of the red or orange dye on each microparticle can be measured by flow cytometry. In one example, the measurement device is a Becton Dickinson FACScan flow cytometer. The microparticles within the population can be classified into clusters based on the intensities of the red and orange dyes on individual microparticles. As shown in FIG. 1, each filled oval dot represents a cluster of microparticles that are commonly labeled with the specified intensities of red and orange dyes. Microparticles within one cluster are distinct from those within each other cluster because they are labeled with different intensities of the red dye, the orange dye, or both the red and orange dyes.

Figure 2:
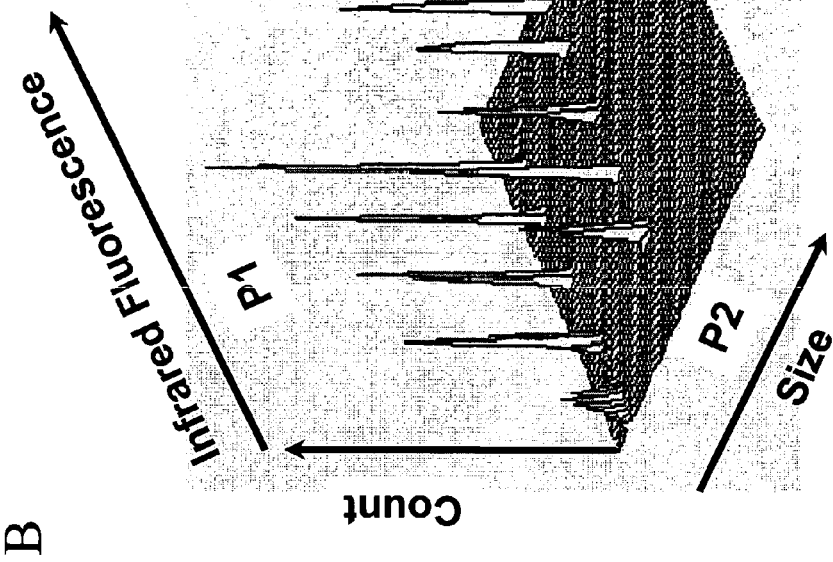
FIG. 2A illustrates how a signature array of a population of heterogeneous microparticles is constructed from the clusters of FIG. 1. Note that the signature array includes the counts or relative counts of entities within each of the at least two distinct clusters of entities.
FIG. 2B illustrates a signature array of a population of microparticles comprising ten (10) distinct clusters of microparticles classified into clusters by two discretely measurable common properties (i.e. their apparent size and relative infrared fluorescent intensity).
Figure 2:
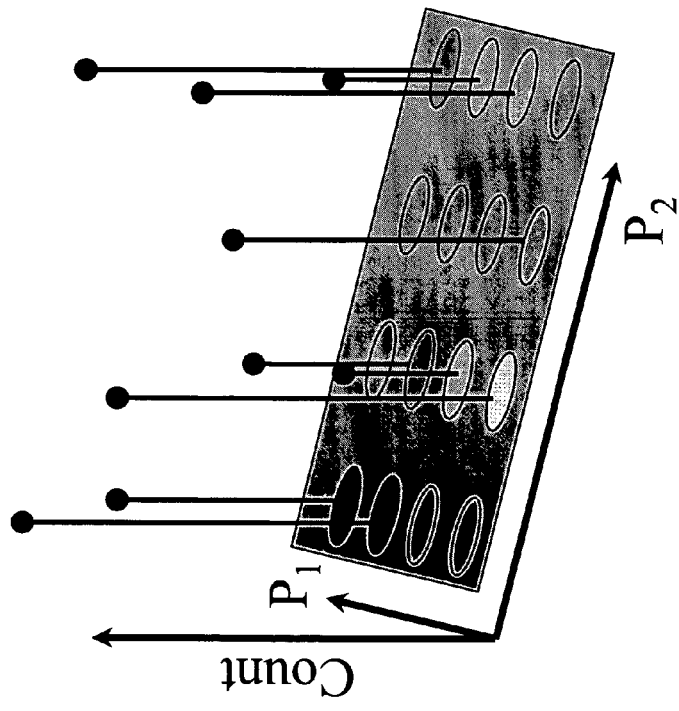

As used herein, "a signature array of a population of entities" is an array comprising information about the counts or relative counts of entities of at least two distinct clusters of entities within the population. Illustrated in FIG. 2A is a signature array of a population of microparticles comprising the clusters of FIG. 1. The signature array comprises information about the counts of microparticles (Z-axis) within each distinct cluster of the population (oval dots). Each cluster is different from one another by at least one distinct discretely measurable common property P1 (X-axis) or P2 (Y-axis), or both P1 and P2. FIG. 2B is a signature array measured from a population of microparticles comprising ten (10) distinct clusters that are distinct from each other by at least size, infrared fluorescent intensity, and/or both, of the particles within each cluster.

The existence of a signature array for a population of entities provides a method of authenticating a product, for example a pharmaceutical product, which is easy to operate, but difficult to imitate or counterfeit. The method of authentication uses a product authentication code defined by a signature array of a population of entities, which has high per volume information content.

As used herein, a "product authentication code" or "product identification code" is a system that represents information specific to a product. The system or code is matched with a particular product or batch of products such that tacking or sampling of the code associated with the particular product or batch of products provides those individuals designated by the source originator of the code or the commercial user of the code to know any of a variety of characteristics or information about the product(s). For example, a "product authentication code" for a pharmaceutical product can represent information about the product, such as the chemical composition, the concentrations of the effective ingredients, the date or place of manufacture, the source of distribution, the batch, the shelf life, or a myriad of other information designations.

A "product authentication code" establishes the product's authenticity and provides a method for tracing the product in the supply chain. A "product authentication code" also addresses re-importation issues, e.g., where a product, for example an HIV drug, is sold outside the developed world under license conditions that preclude sale of licensed products back into the developed world. It can further be used in forensic toxicology to unequivocally identify use/misuse of a product and defend against baseless liability claims, etc.

It is readily appreciated that the present invention encompasses a vast number of product authentication codes depending on the number of clusters and the number of counts per cluster in the signature array. That is, varying the quantity or quality of entities within a population of entities results in a different signature array, thus a different product authentication code.

In some embodiments, different product authentication codes can be obtained by varying the combination of clusters of entities within the population of entities. Different clusters having different discretely measurable common properties are useful in creating different populations of entities, thus different signature arrays and different product authentication codes. For example, microparticles tagged with two different fluorescent dyes can be classified into different clusters based on different amounts of one or both of the two dyes. Various combinations of clusters of microparticles yield various populations of heterogeneous microparticles that can be used to encode various product authentication codes.

In other embodiments, different product authentication codes can be obtained by varying the counts of entities within clusters of the population of entities.

In yet other embodiments, different product authentication codes can be obtained by varying both the composition of clusters that form the population of entities and the counts of entities within one or more clusters.

It is readily appreciated that there is a high per volume information content within the signature arrays of this invention. Thus, the myriad of codes that may be encoded by these signature arrays is very great, limited only by Poisson counting statistics.

In one embodiment, entities with two discretely measurable properties, $P_1$ and $P_2$, can be classified into M clusters, as follows: $M=N_{P1} \times N_{P2}$, where N=number of discrete measurable levels for each property, $P_1$ or $P_2$. In general, the sum of all of the combinations of unique product authentication codes that can be created, I, from a data matrix of M clusters is: $I=2^M-1$, i.e., all possible combinations less the one instance where no cluster is represented in the array. In an illustrative embodiment, e.g., where $N_{p1}$ and $N_{p2}$ each=5, M=25 clusters of entities that can be obtained in this invention. From the 25 clusters, there are $I=2^{25}-1=33,554,431$ (i.e., approximately $3 \times 10^7$) possible unique product authentication codes generated by simply varying the combinations of the clusters to form the population of entities.

In another embodiment, R discretely measurable properties, $P_1, P_2, \ldots, P_R$, can be combined to yield a data matrix or data array with M clusters, as follows, $M=N_{P1} \times N_{P2} \times \ldots \times N_{PR}$, where N is as defined supra. Therefore, the sum of all the combinations of unique product authentication codes that can be created, I, from a data matrix of M clusters is $I=2^M-1$. Thus, with R=3 measurable properties and $N_{P1}$, $N_{P2}$, and $N_{P3}$ each equal to 5, M=125. Then, the number of possible unique product authentication codes is approximately $4 \times 10^{37}$.

In another embodiment, certain cluster(s) may be reserved to identify specific attribute(s) of the product, while other clusters in the population may be used in combination to create codes identifying attributes of the product that are expected to vary, such as production lot number. In this case, the sum of all the combinations of unique lot codes that could be generated from a data matrix of M clusters is: $I=2^{(M-K)}-1$, where K is the number of clusters always occupied or fixed for the product identifier. Thus, for a 25-cluster data array and where K is a set equal to 5, there are still 1,048,575 (i.e., approximately $1 \times 10^6$ or 1 million) possible unique lot identification codes.

In yet another embodiment, $C_{Ln}/C_{Ref}$, the ratio of count of entities within a cluster ($C_{Ln}$) relative to that within a reference cluster ($C_{Ref}$) or the absolute count of entities within a cluster, $[C_{Ln}]$, is used as a measured parameter, $P_C$. In the general case, $P_C$ expands the number of additional unique identifiers as follows: $I=(Nc+1)^{(M-K)}-1$, where $N_C$=number of statistically-distinguishable discrete ratios per cluster or absolute count levels that may be measured practically corresponding to a cluster, and M and K are as defined supra. Thus, from 25 clusters of entities, and where K is a set equal to 5 as above, 3 discrete ratios or absolute count levels for $N_C$ yields 1,099,511,627,775 (i.e., approximately $1 \times 10^{12}$ or 1 billion) possible unique lot identification codes.

In yet another embodiment, once the ratios for each cluster are specified, the total count of all entities per unit volume or unit weight of all clusters is used as a measured parameter, $P_{Tot}$. In the general case, $P_{Tot}$ expands the number of additional unique identifiers as follows: $I=N_{tot}*((Nc+1)^{(M-K)}-1)$, where $N_{Tot}$=number of statistically-distinguishable discrete total count levels per unit weight or unit volume that may be measured practically summed across all clusters in a population of entities. Thus, from 25 clusters, where K is a set equal to 5, and 3 discrete ratios or absolute count levels for $N_C$ exist, as above, if $N_{Tot}$ has just 4 levels, more than 4 billion unique lot identification codes are possible.

In the foregoing embodiments, values selected for R, M, K, $N_C$, and $N_{Tot}$ are selected for purposes of illustration only, and are not meant to be limiting of the practical range of values that may be achieved for the corresponding parameters. That said, these examples demonstrate that signature arrays of a population of entities will accommodate a large amount of information.

One general aspect of the invention is a system that comprises information related to product authentication. Information related to a product authentication code can be recorded, preferably stored in a database, and more preferably in a secured computer database. Information related to signature array can include, for example, the composition of the population of entities used to mark the product for authentication, the discretely measurable common properties of the distinct clusters of entities used to generate the signature array encoding the product authentication code, and optionally, the expected count or relative count of entities within each of the distinct clusters, etc. Information related to a product authentication code can include the information represented by the product authentication code, such as the chemical composition, the concentrations of the effective or active ingredients, the date or place of manufacture, the source of distribution, the batch number, or the shelf life, etc. Such information is readily retrievable, for example, by means of a computer operation. In a preferred embodiment, the system that comprises information related to product authentication is a computer.

Another general aspect of the invention is a method of marking a product for product authentication, comprising the steps of: a) associating a population of entities with the product, wherein the population comprises at least two distinct clusters of entities having detectable counts or relative counts of entities per cluster; and b) assigning a signature array of the population of entities to the product as a product authentication code, wherein the signature array comprises information about the counts or relative counts of entities of at least two distinct clusters of entities within the population.

In a particular embodiment, the method of marking a product for product authentication further comprises a step of correlating the count or relative count of entities within one or more clusters of the population with a specific piece of information about the product, such as the amount, concentration, or presence or absence of a product component.

As illustrated in Example 1 infra, in particular embodiments, fixed information about the product, such as the product identity, the concentration of the active ingredient, and the location of manufacture, etc., can be encoded by fixed array components using identical clusters at fixed counts or relative counts per cluster; and variable information about the product, such as lot number, date of manufacture, date of expiration, etc., can be encoded by variable array components using distinct clusters or identical clusters at distinct counts or relative counts of clusters. A signature array for a product authentication code can comprise a combination of fixed array component(s) and variable array component(s). Thus, distinct signature arrays encoding distinct product authentication codes can have partially identical array components (the fixed array components) and partially distinct array components (the variable array components). Populations of entities used for authenticating distinct products can share partially identical cluster compositions (to encode the fixed array components) and partially distinct cluster compositions (to encode the variable array components).

A wide range of entities are suitable for the present invention, so long as they are compatible with or non-deleterious to the product being marked. Examples of entities that can be used in the present invention, such as microparticles, printed symbols, nucleic acids molecules, or peptides/polypeptides, etc. are described supra.

The product marked can be solid, semi-solid or liquid.

Examples of solid products include pharmaceuticals in tablets, capsules and powders; solid formulations of agrochemicals such as, but not limited to, insecticides, herbicides, fungicides and fertilizers; textiles and leather goods such as clothing and accessories; recordings such as audio and visual recordings including gramophone records, tape cassettes, floppy discs, video cassettes, memory cards, compact discs or other tangible forms of electronic information dissemination; electrical goods such as television sets, computers, DVD players, portable music devices, and radios; motor vehicle components and cameras; paper such as documents, confidential papers, notes, securities, labels, and packaging; chemical products such as inks, biocides, and rubbers; cosmetics such as creams; and food products.

Examples of semisolids include creams, ointments, emulsions and gels.

Examples of liquid products include oil-based products such as lubricating oils, gasoline, diesel and liquified petroleum products; paints; perfumes; cosmetics; beverages including alcoholic beverages; liquid pharmaceutical formulations such as syrups, emulsions and suspensions of one or more drugs; liquid agrochemical formulations; and industrial solvents.

In one preferred embodiment of the invention, the marked product is a pharmaceutical product. The marking of a pharmaceutical product with a product authentication code of the invention can be useful to notify the user, dispenser and/or law enforcement personnel of the composition of the pharmaceutical product enabling the notified parties to determine if the product being tested is the genuine pharmaceutical product from the correct source in the correct concentration.

It will be appreciated that the population of entities can be associated with the product in a wide variety of ways. The population of entities can be present in or on all or part of the product, or in or on all or part of a label, wrapper or container associated with the product. The entities can be incorporated directly into the target product using any suitable technique.

In the case of a drug or chemically active agent, the entities can be formulated in a solid, semi-solid, or liquid, as is known in the relevant art to which the product relates. The entities can be incorporated into a pharmaceutical formulation during the tableting, granulation, spheronization, lyophilization, coating, encapsulation process, or in a combination of any of the aforementioned processes, and the like. For example, the entities can be incorporated in the capsule contents (enteric use) or co-formulated in a tablet (any enteric). For injection formulations, liposome or dye entities can be mixed with the formulation. Alternatively, entities that are insoluble in a hydrophobic solvent, but can be dissolved in an aqueous buffer can also be used for injection formulations. Entities can also be incorporated in the delivery layer of a patch, for example, a transdermal patch.

In some embodiments when the entities are included in the pharmaceutical formulation, the entities are in the pharmaceutical formulation in an amount of below about 0.1% (by weight) of the final formulation. For example, where the entities are a population of microparticles, preferably the microparticles are included in an amount less than 100 ppm, less than 50 ppm, less than 25 ppm, less than 10 ppm or less than 5 ppm of the final formulation.

In certain preferred embodiments where possible and where the entities are added to a pharmaceutical formulation which has already been approved by a governmental agency that regulates pharmaceuticals (such as, for example, the Food and Drug Administration of the United States of America), the entities are included in an amount (e.g., such as an allowable impurity amount) which would not require a re-filing with, or re-approval by, the governmental agency of the pharmaceutical product that has been reformulated to include the heterogeneous population of microparticles. Preferably, the amount of the entities added to the pharmaceutical composition is below the impurity level as provided by the International Conference on Harmonisation (ICH) guidelines.

In other embodiments when the entities are included in the pharmaceutical formulation, the entities are ingestible and/or non-toxic in amounts used.

In another embodiment when the entities are included in the pharmaceutical formulation, the entities are suitable for injection and non-toxic in amounts used. Preferably, when products are intended for use by injection, the ingestible and/or non-toxic entities incorporated in the product do not cause irritation at the injection site or create a risk for peripheral capillary occlusion. Entities made of liposomes or biodegradable substances, such as biodegradable polymers are preferred for injection.

Oral, topical and injectable products of the invention can include solid, semi-solid or liquid delivery systems.

In a particular embodiment, when the entities are included in a liquid pharmaceutical formulation or a formulation to be reconstituted, substantial amounts of the entities can be removed from the pharmaceutical formulation prior to injection or after reconstitution in a liquid, if required. Means such as centrifugation or filtration can be used to remove the entities from the liquid formulation. Alternatively, entities suitable for liquid injection, such as liposomes or their derivatives, can be used to mark an injectable liquid pharmaceutical formulation and the removal of the entities may not be required.

In certain further embodiments, the entities can be associated with the product by being present in the product container, packaging or labeling, or a combination thereof. For example, the population of entities can be applied to the inner, outer, or both inner and outer portions of a container for the pharmaceutical product. The entities can be incorporated into the container during the manufacturing process of the container, and/or the entities can be applied to the inner and/or outer portions of the container or alternatively added during fill. According to this embodiment, the container can take any appropriate form.

In specific embodiments, the entities are included in a label or an article that can be affixed to the container containing the pharmaceutical formulation. For example, where the entities are microparticles, inks containing the microparticles can be used to print the labeling directly onto the container, or printed dots can be printed directly onto the container. Alternatively, printed dots or inks containing the microparticles can be used to print the product authentication code onto a printable article or medium, which can be subsequently applied on a variety of interior and exterior surfaces of the product or the container of the product. Preferably, the printable article is adhesive. Inks, printable articles or media and methods to print microparticles onto a printable article or medium are know to those skilled in the art, see for example, U.S. Pat. No. 5,450,190.

The invention also includes an article that can be affixed to a product, wherein the article comprises a product authentication code of the invention.

For example, the entities can be microencapsulated into a layer of microcapsules, and then applied to the container containing a pharmaceutical formulation. During microencapsulation, very thin coatings of inert natural or synthetic polymeric materials are deposited around the entities to form a layer of microcapsules. The coating material can be chosen from a number of natural and synthetic polymers that is non-reactive with the entities, and is preferably nontoxic. Other components such as, for example, surfactants and plasticizers, may also be added to microcapsules.

The entities can also be affixed on an integrated surface of a pharmaceutical product. For example, the entities can be printed or co-formulated into capsule material (any enteric); co-formulated in the coating of a tablet (e.g., an enteric coating); incorporated into the marking on pre-filled syringes (for injection); or printing on the outer layer of a patch (for a transdermal).

The product authentication code of the invention can be used in combination with one or more other means for product authentication. For example, it can be combined with a radio frequency identification (RFID) tag, spectroscopic inks, hologram, reflective paper, laser etched paper, or a bar code on the package, container or label of the product. It can also be combined with a molecular marker or surface/formulated dye incorporated into the product.

Another general aspect of the invention relates to a product for sale in commerce, wherein the finished product comprises a product authentication code defined by a signature array of a population of entities associated with the product, wherein the signature array comprises information about the counts or relative counts of entities of at least two distinct clusters of entities within the population. In a preferred embodiment, the product is a pharmaceutical product.

Another general aspect of the invention is a method of determining a signature array of a population of entities, comprising the steps of: a) classifying entities within the population into at least two distinct clusters of entities; b) determining the counts or relative counts of entities within each of the at least two distinct clusters; and c) combining the information about the counts or relative counts of entities of the at least two distinct clusters in an array. The population of entities can be associated with a product or exist separately from the product. When the population of entities is associated with the product, it can be either incorporated into the product or associated with the package, container or label of the product.

Depending on the pre-definition or the coding information for the signature array, the array can be detected by measuring the one or more discretely measurable properties of each and all entities within the population of entities, a representative number of entities within the population, or a specific set of one or more clusters of entities within the population.

In certain embodiments of the present invention, the discretely measurable properties of the entities can be measured in the presence of the product. For example, when the population of heterogeneous microparticles is incorporated into a liquid product, the fluorescent intensity of the fluorescent tag associated with the microparticle or the particle size of the microparticle can be measured directly by a flow cytometry measurement of the liquid product.

Figure 3:
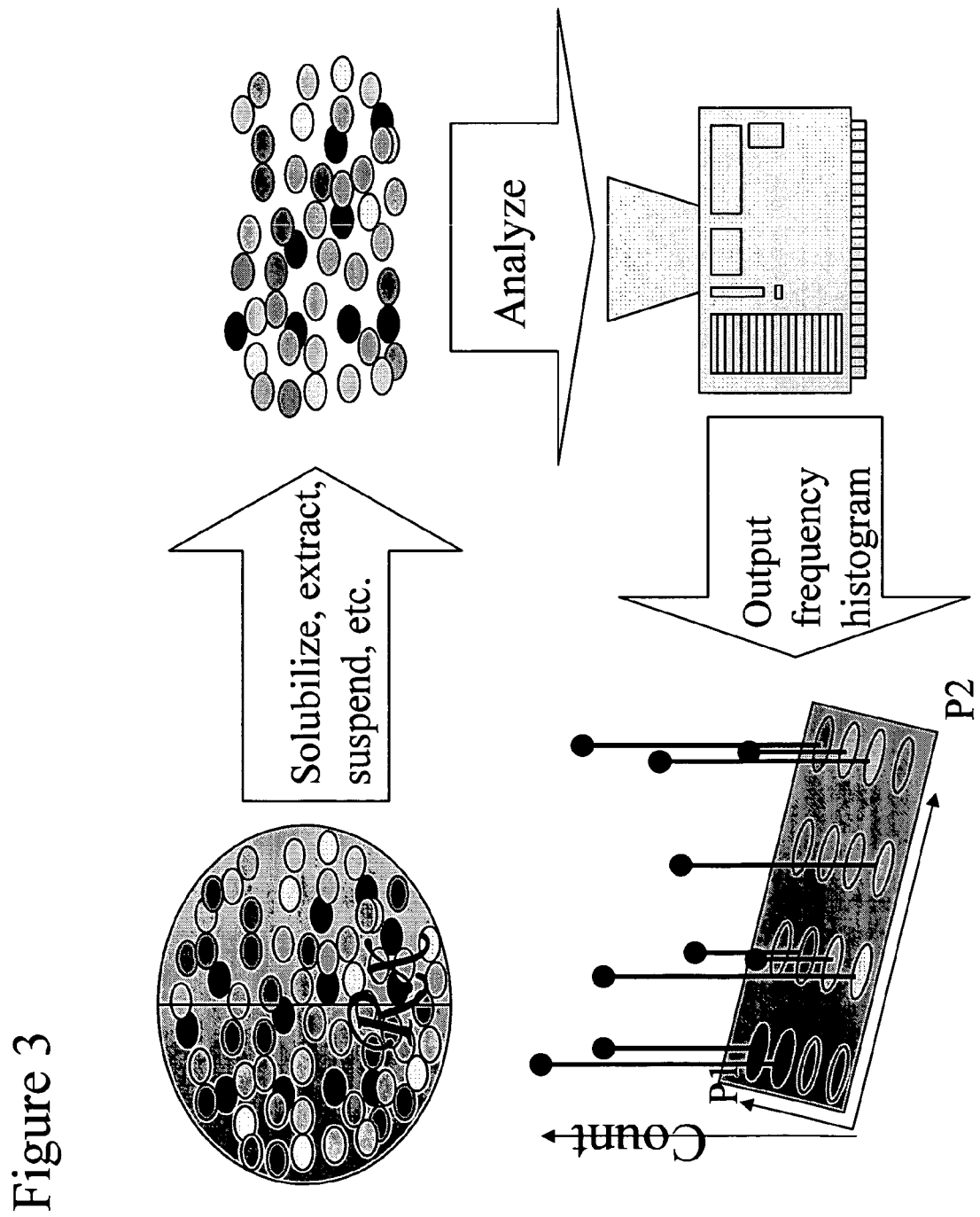
FIG. 3 is a flow chart of the steps for the measurement of the product authentication code of the invention.

In a specific embodiment as illustrated in FIG. 3, when the population of heterogeneous microparticles is incorporated into a solid product, the solid product is first solubilized. The microparticles within the product are extracted, dissolved or suspended in a solvent. The discretely measurable properties of microparticles can then be analyzed, for example, by using a flow cytometer or the like. Alternatively a static cytometer like the CELLSPOTTER® Analyzer from Immunicon can be used as the analyzing device. Preferably, the analyzing device (analyzer) is small and handheld. The analyzer can measure the discretely measurable properties of the microparticles, plot the measured properties in a signature array, and preferably compare the signature array with a saved expected value or values.

Those of ordinary skill in the art will recognize that flow cytometry, is used by way of example only, because it can be applied to assess information associated with the entities of the present invention. The skilled artisan will also recognize that there are a variety of methods to assess information associated with the entities of the present invention.

In some embodiments, the method of the invention further comprises a step of collecting some or all of the population of entities, such as the microparticles. In one embodiment, when the microparticles are associated with the label or container of the product, the microparticles can be collected by many standard techniques. For example, they can be rinsed off the container or label. In the case where the microparticles are microencapsulated into a layer of microcapsules, the layer of microcapsules can be peeled off from the label or container and dissolved or reconstituted, if necessary, to release the encapsulated microparticles. In a specific embodiment, the population of heterogeneous microparticles is incorporated into a coating that is soluble in aqueous solvents.

In another embodiment, when the microparticles are incorporated into the product, the microparticles can be collected by standard means such as centrifugation. The microparticles can also be collected by specific properties associated with the microparticles, such as the physical or chemical characteristic of the particles, magnetic, lipophilic, hydrophobic, or charge property of the particles. In a particular embodiment, WO2004063752 discloses a method for separating or quantitatively determining target particles in a sample. The method changes the amount of charge on the surface of the particles and utilizes the changed charge for separation and quantitative determination of the particles. Such a method can be used in the present invention to collect the microparticles that are incorporated into the product.

In some situations, microparticles tend to form agglomerates when being mixed into a liquid. Effective means of deagglomerating and dispersing can be used to overcome the bonding forces among microparticles after wetting or reconstitution. Such means include, but are not limited to, deagglomerating treatment with ultrasound, rotor stator mixers (e.g. ultra turrax), piston homogenizers, gear pumps or beat mills, colloid mills or ball mills.

In some embodiments, multiple discretely measurable properties of the entities within a population can be measured by a single measurement. For example, the discretely measurable properties of each microparticle within the population, such as the intensity of a dye, including a fluorescent dye associated with the particle, the number of particles, or the particle size of particles, can be obtained from a single flow cytometry measurement of the population of heterogeneous microparticles. The measured properties can then be plotted using readily available computer software programs.

The simultaneous measurement of two or more discretely measurable properties of the entities is preferred when there is a concern that other components present in the environment of the entities may interfere with the specific measurement of the discretely measurable properties of the entities. For example, where flow cytometry is used, the normal range (2-200 μm) of formulation components of a drug may interfere with the laser light scatting particle size analysis of the particles that form a product identification code incorporated into the drug. However when the measurement is set to detect the size of particles having a certain fluorescent tag, the interference from the formulation components is minimized because the formulation components lack the fluorescent tag and will not be measured.

Those of ordinary skill in the art will recognize that populations of heterogeneous entities can be labeled with tags that can be measured with acceptable levels of interference from product formulation components, that can be separated from interfering product components by convenient means, or that have a combination of the forgoing properties.

The discretely measurable properties of the entities can be measured by methods known to those skilled in the art. For example, laser scanning cytometry or flow cytometry is routinely used for simultaneous measurement of multiple properties of a microparticle, such as the size or shape of the particle, or fluorescence signals derived from a fluorophore or plurality of fluorophores associated with the particle.

In flow cytometry, particles are introduced into the center of a fast moving fluid stream and forced to flow single file out a small diameter orifice at uniform speeds. The particles are hydrodynamically focused to the center of the stream by a surrounding layer of sheath fluid. The particles within the stream pass a measurement station where they are illuminated by a light source and measurements can be made at rates of $2.5 \times 10^2$ to $10^6$ particles per minute. Laser light sources are used in the measurement of particles. Typical laser light sources used include argon ion lasers (UV, blue and green light), krypton lasers (yellow and red light), helium-cadmium lasers (UV and blue light), and helium-neon lasers (red light).

A preferred flow cytometer is capable of selecting for the detection of target-correlated signal associated with particles having a defined range of forward-angle and right-angle scattering signal intensity or particular fluorescence (see for example, Yang, et al. *Blood* 81, 1083 (1993), Barker et al. *Blood* 83, 1079-1085 (1994), Fulton et al., *Clin Chem* 43:1749-56(1997), Fulwyler et al., *Methods Cell Biology* 33: 613-29 (1990), and McHugh, *Methods Cell Biology*, Second Edition, Academic Press, v 42, 575 (1994)). Data acquisition is initiated by light scattering and/or fluorescence associated with a particle. Selecting for signal associated with a particle enables the detection of target-correlated signal without interference from fluorescence originating from the bulk solution phase in which the particles are immersed. Thus, the signal/ noise ratio is large. Target-correlated signal is proportional to the amount of target, and determination of multiple target nucleic acids is also possible using the preferred flow cytometric methods. Multiplex analysis of nucleic acids that are free in solution using flow cytometry has been described, see for example, by Fulton et al. (1997), supra, and Fulwyler et al. (1990), supra.

The discretely measurable properties of entities can also be measured by methods utilizing a microscope. Microparticles can be examined manually under a microscope, using a "holder" such as a slide, a hemacytometer chamber, or a Nageotte chamber (also a volumetric analysis). Indeed, many pharmaceutical products have size specifications that were first laid down using microscopy. A typical specification would be for 95% of particles to be less than a specific size (e.g. 50 microns). This would be tested by a skilled technician dispersing a sample on a slide then counting microparticles against a calibrated eye piece reticle.

Microparticles can also be examined automatically or semi-automatically using a static cytometer by scanning. Here the objective field is moved over a fixed stage or using an automated stage, wherein the field is moved past a fixed objective. An example of a static cytometer is the CELL-SPOTTER® Analyzer from Immunicon (a semi-automated fluorescence microscope that enumerates and differentiates between the immuno-magnetically selected microparticle based on fluorescence signals).

The discretely measurable properties of entities can also be measured using a COULTER COUNTER. In a COULTER COUNTER chamber, entities like microparticles suspended in a weak electrolyte solution are drawn through a small aperture separating two electrodes between which an electric current flows. The voltage applied across the aperture creates a "sensing zone". As each entity passes through the aperture (or "sensing zone") it displaces its own volume of conducting liquid, momentarily increasing the impedance of the aperture. This change in impedance produces a tiny but proportional current flow into an amplifier that converts the current fluctuation into a voltage pulse. The Coulter Principle states that amplitude of this pulse is directly proportional to the volume of the entity that produced it. Scaling these pulse heights in volume units enables a size distribution to be acquired and displayed. In addition, if a metering device is used to draw a known volume of the particle suspension through the aperture, a count of the number of pulses will yield the concentration of entities in the sample. The COULTER COUNTER technology can be coupled with optical detection of flow cytometry.

In further embodiments, instruments used for analysis of cells can be adapted to measure the discretely measurable properties of entities using flow cytometry or COULTER COUNTER technology. Such instruments, include, but are not limited to Beckman-Coulter Z1™ Series COULTER COUNTER® Cell and PARTICLE COUNTER (Beckman Coulter, Fullerton, Calif.); PARTEC CYFLOW® SL (Partec, Münster Germany); and Guava Personal Cell Analysis (PCA) System (Guava Technologies, Hayward, Calif.).

Other types of technologies that can be used to measure the discretely measurable properties of entities include the particle counters and particle sizers that are commercially available from Particular Sciences (Dublin, Ireland). "Particle Counters" are the instruments that count entities that are present in a given sample (usually by volume or weight). In contrast, most "Particle Sizers" detect entities present over wide size ranges and return the relative percentages of events within specified size intervals. The discretely measurable properties of entities can be measured using air particle counters with laser detection systems, which are used in clean rooms and hospitals to test the levels of particles from about 0.3~10 microns to certain standards (class 10, 100 etc); or liquid particle counters with light obscuration detectors, which are used in the micron size range and frequently used to test to standards (USP). Laser sensors enable one to count particles below a 1 micron limit. Liquid counters are used with aqueous samples, injectables and with oils used in industry. More detail is obtainable from the company web site of Particle Measuring Systems, Inc (Boulder, Colo.).

One other general aspect of the present invention is a method of authenticating a product, comprising the steps of: a) associating a population of entities with the product, wherein the population comprises at least two distinct clusters of entities having detectable counts or relative counts of entities per cluster; b) assigning a signature array of the population of entities to the product as a product authentication code, wherein the signature array comprises information about the counts or relative counts of entities of at least two distinct clusters of entities within the population; wherein information about the signature array and the product authentication code is recorded; c) analyzing the product to obtain a measured signature array of the population of entities associated with the product; d) comparing the measured signature array with that which is expected based on the recorded information; and e) accepting the product as authenticate when the measured signature array matches that which is expected.

The authentication method begins with marking a product with a product authentication code of the present invention. The information associated with the product authentication code and the information about the particular signature array that encodes the product identification code is recorded. Based on the recorded information, an authorized person would expect to find a certain signature array based on certain product information, or certain product information based on the detection of a certain signature array associated with the product. To confirm whether a product in commerce is authentic, an authorized person, based on knowledge from the record, will readily know what particular signature array is expected to be detected from the product. After determining the signature array associated with the product using methods described supra, the authorized person will compare the measured signature array with what is expected based on the recorded information. A match of the measured signature array with that which is expected, taking into account of the experimental errors of the measurements, indicates that the product in commerce is authentic.

The experimental errors of the measurement can result in uncertainty about whether the measured signature array indeed matches that which is expected. To increase the level of confidence, multiple signature arrays may be associated with a single product, optionally, at, on or within different portions of the product to allow multiple measurements and comparisons of the measured signature arrays with that which is expected. The multiple signature arrays can be identical or distinct.

In an illustrative embodiment, even a simple dilution of the product can be detected by the reduced microparticle count per unit volume of each cluster on a signature array of the population of microparticles associated with the product.

Because a product authentication code of the invention can encrypt product (or active ingredient) concentration information, the product authentication code can be used as a surrogate for direct analytical measurement, eliminating costly analytical steps in manufacturing quality control. Therefore, the invention also provides a method for quality control and release of products from a manufacturing process, comprising the steps of: a) associating a population of entities with a product during the manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) analyzing the product to obtain a measured signature array of the population of entities associated with the product; c) comparing the measured signature array with that which is expected based on the recorded information; and d) releasing products manufactured by the manufacturing process when the measured signature array matches that which is expected. In a preferred embodiment, the product is a pharmaceutical product.

In a particular embodiment, the population of entities or a cluster of the population is incorporated into an ingredient or component of the product during the manufacturing process. Thus, the presence of the expected signature array or information about the cluster detected from the product is indicative of the presence and quantity of the ingredient or component in the product.

The invention further includes a product manufactured by the process of manufacturing using the product authentication code as a surrogate for direct analytical measurements.

This invention will be better understood by reference to the examples that follow. Those skilled in the art will readily appreciate that these examples are only illustrative of the invention and not limiting.

Example 1

Authenticating PROCRIT Liquid Formulation Using Fluorescent Microparticles

This Example illustrates a method of the present invention for product authentication using a population of heterogeneous microparticles to label a pharmaceutical product having a liquid formulation. In particular, this Example illustrates a method of product authentication using a population of heterogeneous microparticles to label the liquid pharmaceutical product PROCRIT, wherein each microparticle within the population is labeled with one of two different fluorescent dyes. Similar methods can also be used to authenticate other liquid formulation products.

Microparticles labeled with fluorescent dyes were purchased from Invitrogen Corporation (Carlsbad, Calif.) to be used as a heterogeneous population of entities. Individual vials of microparticles from LINEARFLOW flow cytometry intensity calibration particle kits were obtained as follows: Deep Red 2.5 µm (L14818; lot#38976a), Deep Red 6 µm (L14819; lot#39308a), Green 2.5 µm (L14821; lot#21833w), and Green 6 µm (L14822; lot#41635a). These particles were labeled by the manufacturer with different dyes: a fluorescent dye at 633 nm excitation/660 nm emission (Deep Red, Dye1) and a fluorescent dye at 488 nm excitation/515 nm emission (Green, Dye 2) respectively. Each kit contained six vials of polystyrene particle suspensions stained with the corresponding dyes at different intensity levels that were visualized as six discrete peaks on a fluorescence histogram when analyzed using a Becton Dickinson FACSCALIBER flow cytometer and CELLQUESTPRO analysis software.

The three suspensions with the highest fluorescence intensity from the 2.5 µm sets (D, E, and F) and the four suspensions with the highest fluorescence intensity from the 6 um sets (C, D, E, and F) were used as clusters of entities to prepare heterogeneous populations of entities according to the volumes given in Table 1.

TABLE 1a

Populations of Invitrogen microparticles comprising 7 clusters

|  | G1 (µl) | R1 (µl) | G2 (µl) | R2 (µl) |
|---|---|---|---|---|
| 2.5 µm Suspension D | 100 | 100 | 200 | 200 |
| E | 200 | 200 | 100 | 100 |
| F | 100 | 100 | 200 | 200 |
| 6 µm Suspension C | 200 | 200 | 100 | 100 |
| D | 100 | 100 | 200 | 200 |
| E | 200 | 200 | 100 | 100 |
| F | 200 | 200 | 200 | 200 |
| Total Volume | 1100 | 1100 | 1100 | 1100 |

TABLE 1b

Populations of Invitrogen microparticles comprising 14 clusters

|  | G1/R1 (µl) | G1/R2 (µl) | G2/R1 (µl) | G2/R2 (µl) |
|---|---|---|---|---|
| G1 | 400 | 400 |  |  |
| R1 | 400 |  | 400 |  |
| G2 |  |  | 400 | 400 |
| R2 |  | 400 |  | 400 |
| Total Vol | 800 | 800 | 800 | 800 |

G = LINEARFLOW Green particles (2.5 µm @ 4.6e10$^7$ particles/ml; 6 µm @1.9e10$^7$ particles/ml).
R = LINEARFLOW Deep Red particles (2.5 µm @ 4.6e10$^7$ particles/ml; 6 µm @2.1e10$^7$ particles/ml).

Each of the populations of microparticles according to Table 1b, G1/R1, G1/R2, G2/R1, and G2/R2, contains 14 distinct clusters of entities. These populations were analyzed based on differences in particle size and fluorescent label by flow cytometry (FACS) using the FACSCALIBER.

PROCRIT (Epoetin Alpha; lot#P004839; Amgen\Ortho-Biotech) was selected as a representative commercial pharmaceutical product. Twenty-five (25) microliters of each of the four mixtures shown in Table 1b (labeled G1/R1, G1/R2, G2/R1, and G2/R2) was added separately to each of four 1-ml vials of PROCRIT, then mixed by vortexing. Each of the four vials was then labeled with the population name and numbered 1 through 4. One hundred (100) microliters of samples was removed from each of the four vials and mixed 1:1 with 100 µl Dulbecco's Phosphate-buffered Saline without Ca$^{++}$ or Mg$^{++}$ (DPBS; Cellgro) in a 12×75 mm polystyrene tube (Falcon) for analysis on the FACSCALIBER. The remainder in the vials was returned to 4° C. Subsequent readings were taken on days 2, 7 and 14 using undiluted sample aliquots. Each of the four input populations according to Table 1b, G1/R1, G1/R2, G2/R1, and G2/R2, was also directly measured as daily input controls (5 µl freshly added to 200 µl DPBS). The measured results from the samples were then compared to the measured input ratios (i.e., the mean determination from multiple replicate determinations of the input populations) to confirm whether or not the product was authentic.

Figure 4:
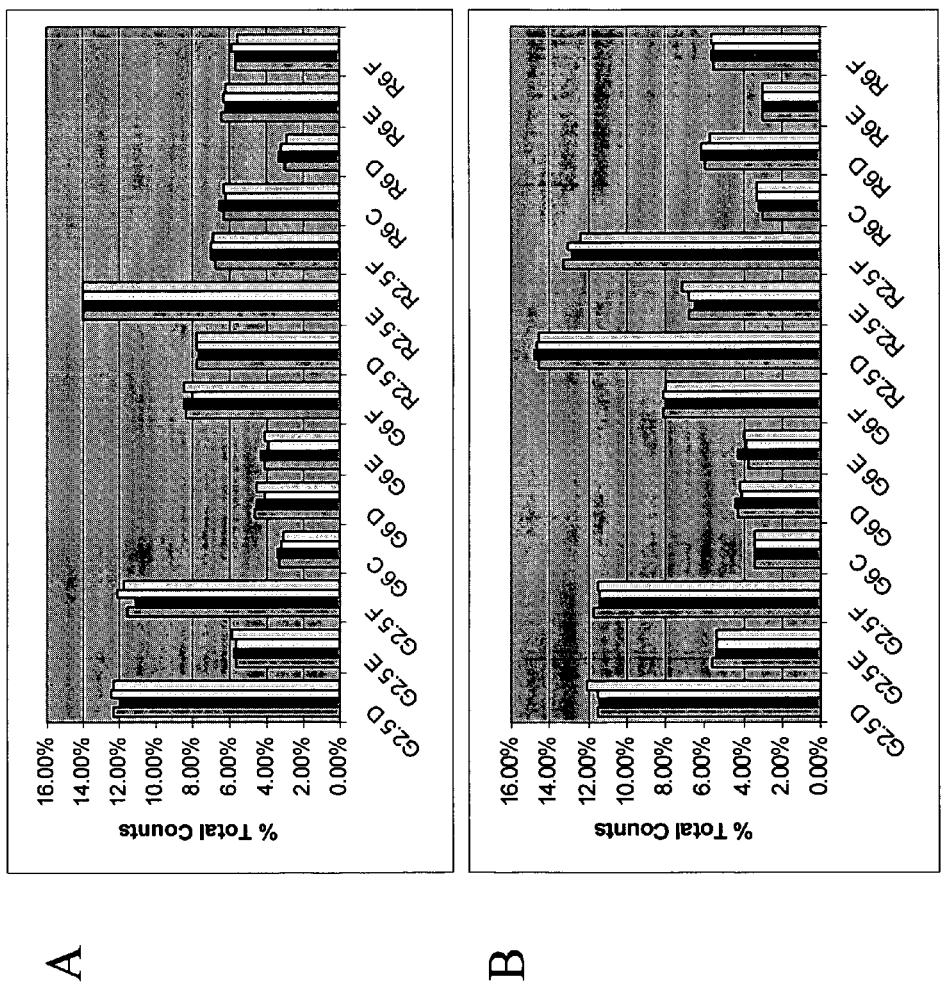
FIG. 4 shows that two different signature arrays created in replicate and measured from two sub lots of PROCRIT were reproducible and distinct.

FIG. 4A shows that the signature array measured from PROCRIT sample lots containing the G2/R1 population was reproducibly incorporated into this liquid product. Listed in the X-axis are the 14 distinct clusters within the G2/R1 population. For each cluster, the four bar plots represent the relative counts of entities measured from replicate preparations of PROCRIT into which the G2/R1 population was incorporated. Likewise, FIG. 4B shows similar results for the signature array measured from PROCRIT sample lots containing the G2/R2 population. A comparison of FIG. 4A and FIG. 4B shows that the G2/R1 and G2/R2 populations share identical "G" components of the arrays (G2.5D, G2.5E, G2.5F, G6C, G6D, G6E, G6F) but distinct "R" components of the array (R2.5D, R2.5E, R2.5F, R6C, R6D, R6E, R6F). It illustrates that signature arrays can be designed to encode fixed information associated with fixed array components (for example, product identity, concentration, etc. associated with the G components of the array) and variable information associated with variable array components (for example, lot number, date of manufacture, etc. associated with the R components of the array). Similar results were also observed with the samples containing the G1/R2 and G2/R2 signature arrays (data not shown). Signature arrays measured on day 1 from sample lots labeled with either one of the four populations G1/R1, G1/R2, G2/R1, and G2/R2 were indistinguishable from that measured on subsequent days 2, 7, and 14 (data not shown).

Example 2

Authenticating TYLENOL Sore Throat Liquid Suspension Using Fluorescent Microparticles In this Example, the liquid pharmaceutical product Extra-Strength TYLENOL Sore Throat ("Sore Throat", lot # RKG; McNeil Pharmaceuticals) was chosen for product authentication using spherotech particle arrays. It is readily recognized that this product is chosen by way of example and that any liquid product or product that may be reconstituted or dissolved in liquid, whether for pharmaceutical applications or other applications, could be used, according to this example.

Sore Throat contains dye and ingredients, including polyethylene glycol, propylene glycol, and sucrose, that increase product viscosity. To construct a signature array that is compatible with the potential interfering components of Sore Throat, we used polystyrene microparticles purchased from Spherotech Inc. (Libertyville, Ill.), as follows: Blue 5.1 µm (PAK-5067-10K; lot#U01) and Blue 7.7 μm (PAK-7067-9K; lot#X01) SPHERO fluorescent particle array kits. Each kit contains individual particle suspensions (10 and 9 respectively) stained with blue fluorophores at different intensity levels that could be resolved into analytically distinct clusters based upon fluorescence and light scatter properties when analyzed on the FACSCALIBUR flow cytometer and CELLQUESTPRO analysis software.

Particle counts in each vial of Blue 5.1 μm (about $1e10^8$) and Blue 7.7 μm (about $1e10^7$) were determined by hemacytometer count. Aliquots from each particle suspension were taken and diluted in microfuge tubes (Eppendorf) 1:100 for the Blue 5.1 μm and 1:10 for the Blue 7.7 μm using distilled water. These samples were then vortexed and particle counts obtained by loading 10 μl from each onto duplicate chambers of a 9 $mm^2$ hemacytometer (Reichert; Buffalo, N.Y.). Manual counts were made under 10× power from a single millimeter square at the center of each chamber grid using a light microscope (Zeiss; West Germany). The average of the two counts was used to calculate the final counts. Note that all samples were vortexed immediately prior to loading onto the hemacytometer to ensure that particles were equally distributed in the suspension before counting.

Signature arrays with particle count targets as shown in Table 2 were designated for lots 2a, 2b, 3a, 3b, 4a and 4b of Sore Throat. Clusters 1 to 11 (excluding 5 and 9) are represented by Blue 5.1 μm microparticle suspension peaks 2 through 10, respectively, and clusters 13 to 22 (excluding 16 and 17) are represented by Blue 7.7 μm microparticle suspension peaks 2 through 9. Without limiting the number of other additional clusters that could be included in the arrays, excluded Clusters 5, 9, 16, and 17 are shown in the table as placeholders for such additional clusters. As an internal reference, Cluster 22 was added at the same count per unit volume in all six codes. Based on the particle count targets and the particle counts in each cluster, the precise volume of each cluster to be used in each signature array was calculated and added to the different lots of Sore Throat. Table 3 lists the precise volume of each cluster used. Note that for clusters 1 to 11, microparticle stocks were diluted 1:10 with DPBS to give the proper starting concentration.

TABLE 2

Designated signature arrays for different lots of Sore Throat

| Cluster Id | Cluster Composition | | Particle Counts ($1e\,10^6/\mu l$) | | | | | |
|---|---|---|---|---|---|---|---|---|
| | | | Lot 2a | Lot 2b | Lot 3a | Lot 3b | Lot 4a | Lot 4b |
| 1 | Blue 5.1 peak | 2 | 200 | | 50 | | 200 | |
| 2 | | 3 | | 50 | | 200 | | 200 |
| 3 | | 4 | 50 | | 200 | | 200 | |
| 4 | | 5 | | 100 | | 100 | | 200 |
| 5 | | | | | | | | |
| 6 | | 6 | 200 | | 25 | | 200 | |
| 7 | | 7 | | 25 | | 200 | | 200 |
| 8 | | 8 | 25 | | 25 | | 200 | |
| 9 | | | | | | | | |
| 10 | | 9 | | 100 | | 100 | | 200 |
| 11 | | 10 | 50 | | 200 | | 200 | |
| 12 | | | | | | | | |
| 13 | Blue 7.7 peak | 2 | | 200 | | 200 | | 200 |
| 14 | | 3 | 50 | | 200 | | 200 | |
| 15 | | 4 | | 200 | | 200 | | 200 |
| 16 | | | | | | | | |
| 17 | | | | | | | | |
| 18 | | 5 | 100 | | 100 | | 200 | |
| 19 | | 6 | | 200 | | 50 | | 200 |
| 20 | | 7 | 100 | | 100 | | 200 | |
| 21 | | 8 | | | | | | |
| 22 | | 9 | 100 | 100 | 100 | 100 | 100 | 100 |
| Total Counts | | | 875 | 775 | 1000 | 1100 | 1700 | 1300 |

TABLE 3

Volumes of clusters to be added to different lots of Sore Throat

| Cluster id | Cluster Composition | | Sample Volume (μl) | | | | | |
|---|---|---|---|---|---|---|---|---|
| | | | Lot 2a | Lot 2b | Lot 3a | Lot 3b | Lot 4a | Lot 4b |
| 1 | Blue 5.1 peak | 2 | 12.3 | 0.0 | 3.1 | 0.0 | 12.3 | 0.0 |
| 2 | | 3 | 0.0 | 7.8 | 0.0 | 31.4 | 0.0 | 31.4 |
| 3 | | 4 | 11.1 | 0.0 | 44.4 | 0.0 | 44.4 | 0.0 |
| 4 | | 5 | 0.0 | 17.8 | 0.0 | 17.8 | 0.0 | 35.6 |
| 5 | | | | | | | | |
| 6 | | 6 | 46.5 | 0.0 | 5.8 | 0.0 | 46.5 | 0.0 |
| 7 | | 7 | 0.0 | 5.6 | 0.0 | 44.7 | 0.0 | 44.7 |
| 8 | | 8 | 5.8 | 0.0 | 5.8 | 0.0 | 46.5 | 0.0 |
| 9 | | | | | | | | |
| 10 | | 9 | 0.0 | 13.9 | 0.0 | 13.9 | 0.0 | 27.8 |
| 11 | | 10 | 8.5 | 0.0 | 34.2 | 0.0 | 34.2 | 0.0 |
| 12 | | | | | | | | |
| 13 | Blue 7.7 peak | 2 | 0.0 | 25.2 | 0.0 | 25.2 | 0.0 | 25.2 |
| 14 | | 3 | 9.2 | 0.0 | 36.7 | 0.0 | 36.7 | 0.0 |
| 15 | | 4 | 0.0 | 46.8 | 0.0 | 46.8 | 0.0 | 46.8 |
| 16 | | | | | | | | |
| 17 | | | | | | | | |
| 18 | | 5 | 14.2 | 0.0 | 14.2 | 0.0 | 28.5 | 0.0 |
| 19 | | 6 | 0.0 | 33.6 | 0.0 | 8.4 | 0.0 | 33.6 |
| 20 | | 7 | 19.0 | 0.0 | 19.0 | 0.0 | 37.9 | 0.0 |

TABLE 3-continued

Volumes of clusters to be added to different lots of Sore Throat

| Cluster id | Cluster Composition | Sample Volume (µl) | | | | | |
|---|---|---|---|---|---|---|---|
| | | Lot 2a | Lot 2b | Lot 3a | Lot 3b | Lot 4a | Lot 4b |
| 21 | 8 | 0.0 | 0.0 | 0.0 | 0.0 | 0.0 | 0.0 |
| 22 | 9 | 22.5 | 22.5 | 22.5 | 22.5 | 22.5 | 22.5 |
| | Total Clusters (µl) | 149.1 | 139.5 | 185.7 | 202.1 | 309.5 | 233.8 |
| | Tylenol/PBS (µl) | 1850.9 | 1860.5 | 1814.3 | 1797.9 | 1690.5 | 1766.2 |

For analysis on the FACSCALIBUR, each sample was diluted 1:10 with DPBS (100 µl sample+900 µl DPBS) in 12×75 mm polystyrene tubes (FALCON) in order to minimize the background effects from Sore Throat. Particles were classified into clusters on the basis of size and fluorescent intensity and normalized as counts relative to reference cluster 22. The balance of the original sample lots were sealed with parafilm (Pechiney Plastic Packaging) and stored in the dark at room temperature. Additional aliquots were analyzed on days 2 and 7 to determine the stability of each array over time. The measured results from the sample lots were then compared to the calculated input ratios (the expected value) to confirm whether or not the product was authentic.

Figure 5:
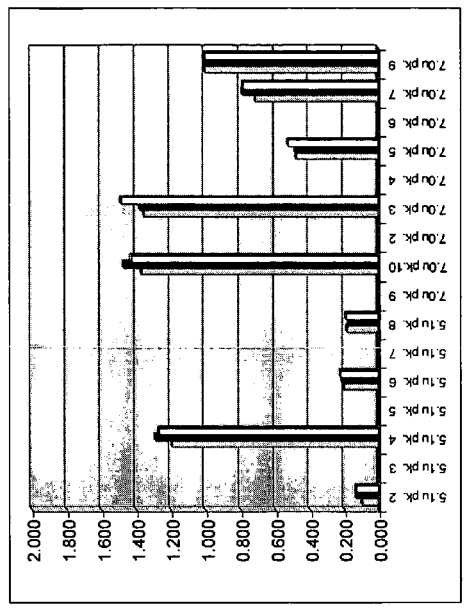
FIG. 5 shows that each of the four (4) different signature arrays measured from four (4) different lots of TYLENOL Sore Throat matched the expected arrays.
Figure 5:
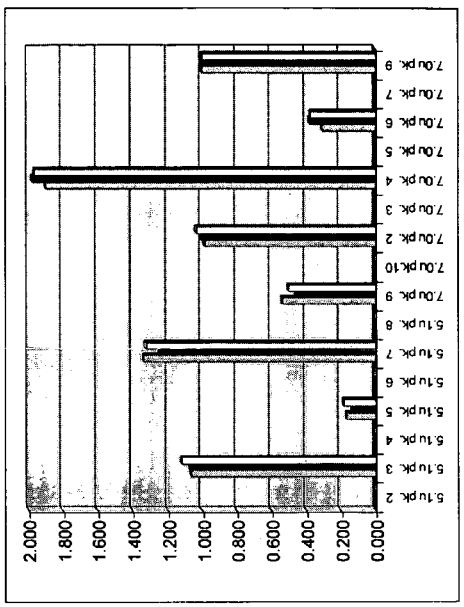
Figure 5:
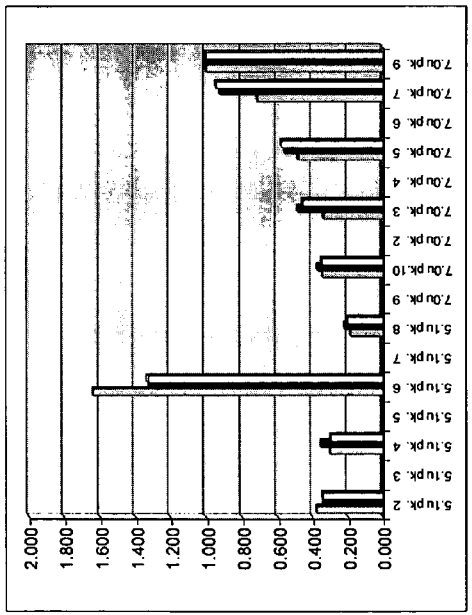
Figure 5:
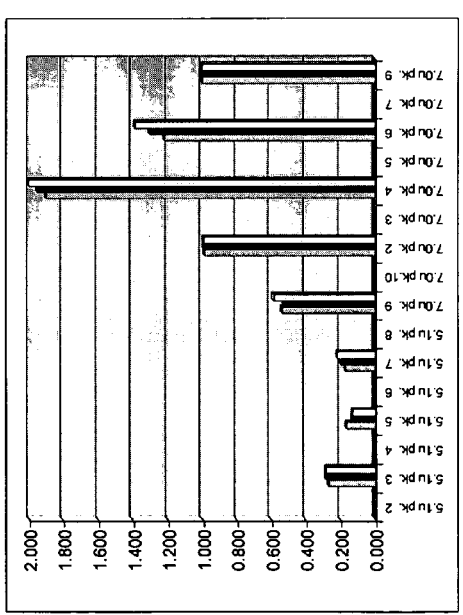

FIG. 5A shows that the signature arrays measured from the Lot 2a Sore Throat matched that which was expected. Listed in the X-axis are 9 distinct clusters within the lot. The Y-axis represents the relative count of particles within a cluster. The relative count was determined by the count of particles within the cluster relative to the count of particles within the reference cluster (comprising the blue 7.7 peak 9 particles). For each cluster, the first bar from the left represents the expected relative counts of particles within the cluster (i.e., the signature array as measured from a PBS control). The second and the third bars from the left represent the measured relative counts of particles obtained from labeled Sore Throat on day 1 and day 2, respectively. Results showed good correlation between the expected array and the measured array. Similar results were also observed with other lots of Sore Throat, such as the Lot 3a, 2b, and 3b, as illustrated in FIGS. 5B, C, and D, respectively.

Those of ordinary skill in the art of pharmaceutical sciences can use microspheres with alternative composition. For example, U.S. Pat. No. 6,773,812 describes hybrid microspheres constructed using fluorescent or luminescent microspheres and magnetic nanoparticles. Additionally, other analytical methods for distinguishing subsets of microspheres can be used, for example, devices like the Immunicon CELLSEARCH instrument.

It is evident to the skilled practitioner that this example employs ingestible labeled particles in the products. However, such products contain only trace amounts of such microparticles. Further, careful choice of dyes will result in consumption of only dye that is otherwise deemed safe for human consumption.

Example 3

Authenticating Solid Formulations Using Fluorescent Microparticles Applied to the Product Surface The methods of this invention are not limited to formulations intended for liquid oral administration. In the present Example 3, the signature array of heterogeneous fluorescent microparticle entities was associated with a pharmaceutical product by application of a coating to the surface of an insoluble tablet formulation, wherein the microparticles used were of two different sizes and labeled with either the same or two different fluorescent dyes. A person skilled in the art can readily appreciate that other coatings for pharmaceutical tablet can be used and that other types of entities can also be used following similar procedures to those of this example.

Tablets were prepared from calcium phosphate ($CaPO_4$; Fuji Chemical) with a sucrose coating in a three-step process: manufacturing of tablets, sugar coating of tablets and application of microbeads. The coating process was performed in a 6-inch pan coater. The first step of the sugar coating process was to pre-condition the coater. This was accomplished by placing a quantity of placebo (microcrystalline cellulose) tablets sufficient to fill the coater for pre-conditioning. Excess sucrose solution was added and the pan rotated until the sides of the coating pan were adequately covered in sucrose. A spatula was used as needed to ensure that the coater was sufficiently covered. The tablets and excess sucrose were discarded and the remaining sucrose in the coating pan was dried. Tablets comprising of dibasic calcium phosphate (FUJICALIN) with magnesium stearate were added to the pre-conditioned coater. These tablets were manufactured using deep concave tooling to make an almost spherical tablet. A small amount of sucrose solution was added to coat the tablets and then they were dried with alternating room temperature air and hot air while rotating in the coating pan. This process was repeated until the tablets were adequately covered with sucrose and dried. The microbead suspension was then mixed using a vortex to obtain a uniform suspension. A measured quantity of the microbead suspension was applied to the surface of individual tablets and dried at room temperature.

Microparticles labeled with fluorescent dyes purchased from Invitrogen Corporation (Carlsbad, Calif.), as more fully described in Example 1, were formulated to yield signature arrays that would match some or all of the values shown in the "Input" column of Table 4, which is the percent of total fluorescent events per fluorescence detector channel on the FACSCALIBUR flow cytometer. Microparticles with "G" events were detected in the FL1 channel and "R" events in the FL2 channel. The signature array of each of the G and R populations was designed to match half of the input values. Thus, the signature array of the G+R population, which was a mixture of the G and R population in equal volume, would match all of the input values.

Each of the G, R, and G+R populations was mixed 5:1 with a solution of saturated sucrose. Six microliters of each mixture was applied to the sucrose-coated surface of an individual test tablet, and left to dry overnight in the dark under ambient conditions. To reveal a characteristic visible mark on the tablet within the simulated logo, the tablets were examined under ultraviolet light. It was observed that tablets applied with G, R, and G+R populations fluoresced visibly in characteristic green, red, and orange light, respectively.

To reveal the underlying signature array information, the tablet was washed with 400 µl DPBS into 1.5 ml microfuge tubes and then centrifuged for 10 minutes at 14,000 rpm in a microfuge. The supernatant was removed from each tube by aspiration until approximately 50 µl fluid remained. One hundred fifty microliters of fresh DPBS/0.1% triton X100 was added back to each sample prior to transfer into separate 12×75 mm polystyrene tubes (FALCON) for FACS. As shown in Table 4, the measured signature arrays corresponding to G, R, and G+R populations matched half or all of the Input values.

TABLE 4

Signature arrays that matched some or all of the Input values

|  | Input | G + R | G | R |
|---|---|---|---|---|
| Green - B | 38.3 | 37.7 | 43.5 | 0.0 |
| C | 9.1 | 8.3 | 7.5 | 0.0 |
| D | 3.5 | 3.9 | 3.3 | 0.0 |
| E | 32.6 | 34.5 | 31.4 | 0.0 |
| F | 16.6 | 15.6 | 14.1 | 0.0 |
| Red - B | 26.5 | 27.7 | 0.0 | 27.8 |
| C | 36.0 | 36.3 | 0.0 | 34.5 |
| D | 8.8 | 9.1 | 0.0 | 9.8 |
| E | 5.8 | 5.1 | 0.0 | 5.6 |
| F | 22.9 | 21.8 | 0.0 | 22.3 |

To test the reproducibility of associating a signature array by the methods of this Example, the population G2/R2 as described in Table 1b of Example 1 was formulated, and mixed 5:1 with a solution of saturated sucrose. Six microliters of said mixture was applied to the sucrose-coated surface of each of six test tablets, then left to dry overnight in the dark under ambient conditions. Three tablets were then washed with 400 µl DPBS per tablet into 1.5 ml microfuge tubes. The other three tablets were washed with 400 µl DPBS/0.1% triton X100. Next, the samples were prepared for FACS analysis as described above.

Figure 6:
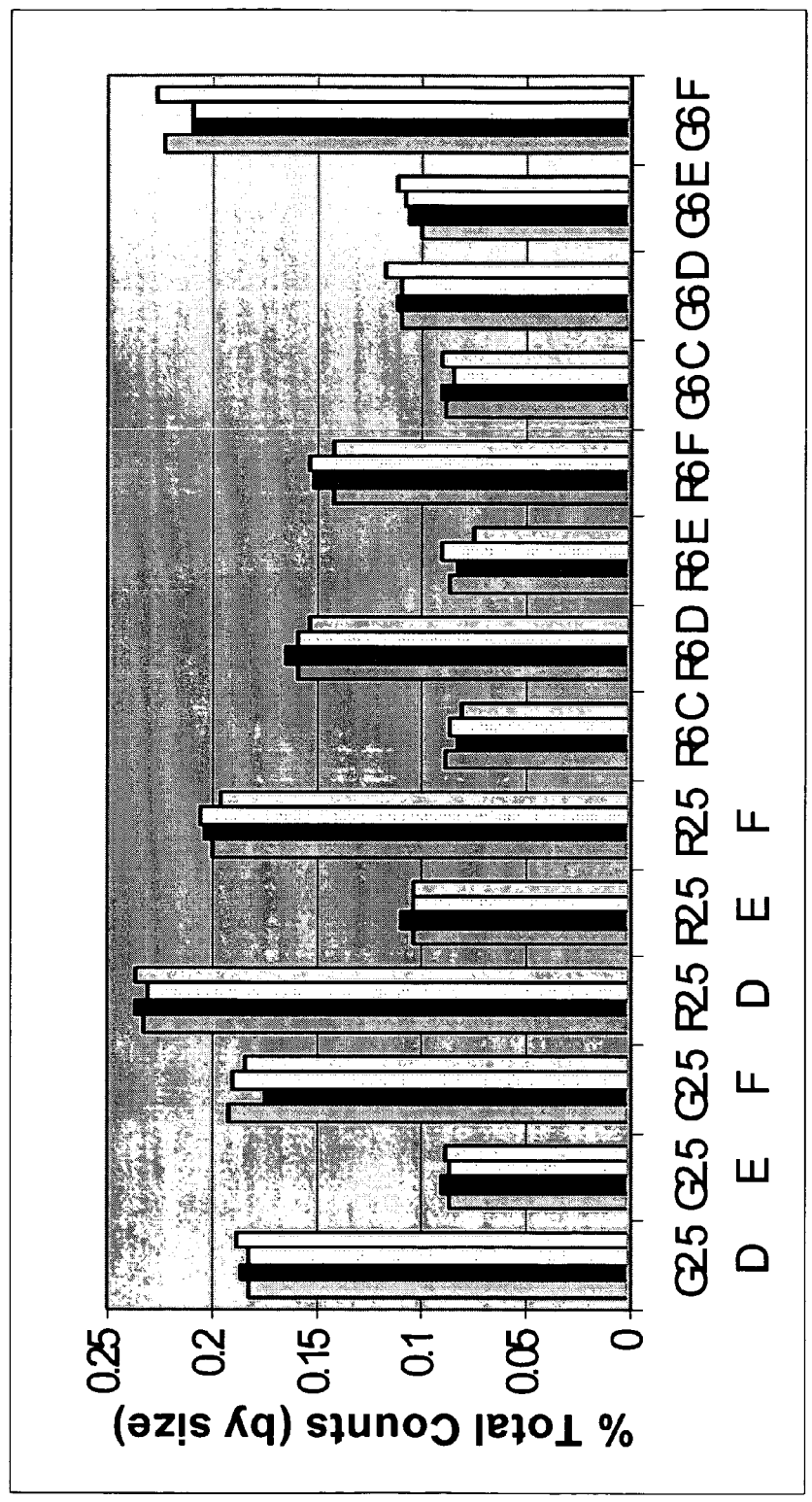
FIG. 6 shows that the signature array measured from a tablet marked with the population G2/R2 on the surface of the tablet matched the expected array.

FIG. 6 shows that the signature arrays measured from the solid formulation containing the population G2/R2 after washing with DPBS matched that from the controls consistently. Listed in the X-axis are the 14 distinct clusters within the G2/R2 population. For each cluster, the first three bar plots from the left represent the relative counts of entities measured from the three tablets; and the fourth bar plot represents the relative counts of entities measured from the G2/R2 population directly, i.e., the population incorporated directly into PBS as a control. The relative count is defined as the count of entities per cluster relative to the sum of counts of entities having the same size, i.e., 2.5 µm or 6 µm.

This Example 3 demonstrates that a signature array can be associated with an article of product by deposition on the article's surface in a way such that both a visible authenticating mark and an invisible signature array can be revealed. Such a signature array can be associated with a logo or other visibly identifying mark, which are commonly placed on the surface of commercial pharmaceutical products. Those of ordinary skill in the art of pharmaceutical sciences recognize that the visible component is not required to achieve association of the signature array using modifications of the method of this Example.

Example 4

Authenticating Solid Formulations Using Fluorescent Microparticles within the Formulation In the present Example, the signature array of heterogeneous fluorescent microparticle entities was associated with articles of pharmaceutical product by incorporating fluorescent microparticle into a table formulation, wherein the microparticles used were of two different sizes and labeled with two different fluorescent dyes.

Tablets were prepared from water-soluble mannitol (200 mg each, Roquette America), as follows. The mannitol tablets with microbeads were manufactured as individual tablets using both standard pilot scale and laboratory equipment. For each tablet manufactured, approximately 200 mg of mannitol (Pearlitol 300 DC) was weighed into a suitable container. The microbead suspension was then mixed using a vortex to obtain a uniform suspension. A measured quantity ranging from 2 µL to 25 µL of the microbead suspension was added to the weighed mannitol. The material was then dried at room temperature in an open container. Each tablet was individually manufactured by pouring the 200 mg of mannitol with the dried microbeads directly into the tablet die and compressing using a 10-station rotary tablet press. The tablet punches were manually lubricated, as needed, by applying magnesium stearate directly to the punch faces. The Tablets included Invitrogen microparticle population G1, G2, R1 or R2 as described in Table 1a of Example 1 in the formulation at each of the following amounts per tablet: 5 µl, 10 µl, 15 µl or 25 µl.

To recover the Invitrogen microparticles, tablets were dissolved separately in 1 ml DPBS/0.1% triton X100 in 1.5 ml microfuge tubes (EPPENDORF) warmed in a hot water bath at approximately 100° C. Once dissolution was complete, samples were centrifuged for 5 minutes at 14,000 rpm in a microfuge. Without disturbing the pellet containing the microparticles, as much of the supernatant as possible was removed by aspiration. Two hundred microliters of fresh DPBS/0.1% triton X100 was then added to each tube and the samples were transferred to 12×75 mm polystyrene tubes (FALCON) for FACS analysis.

Figure 7:
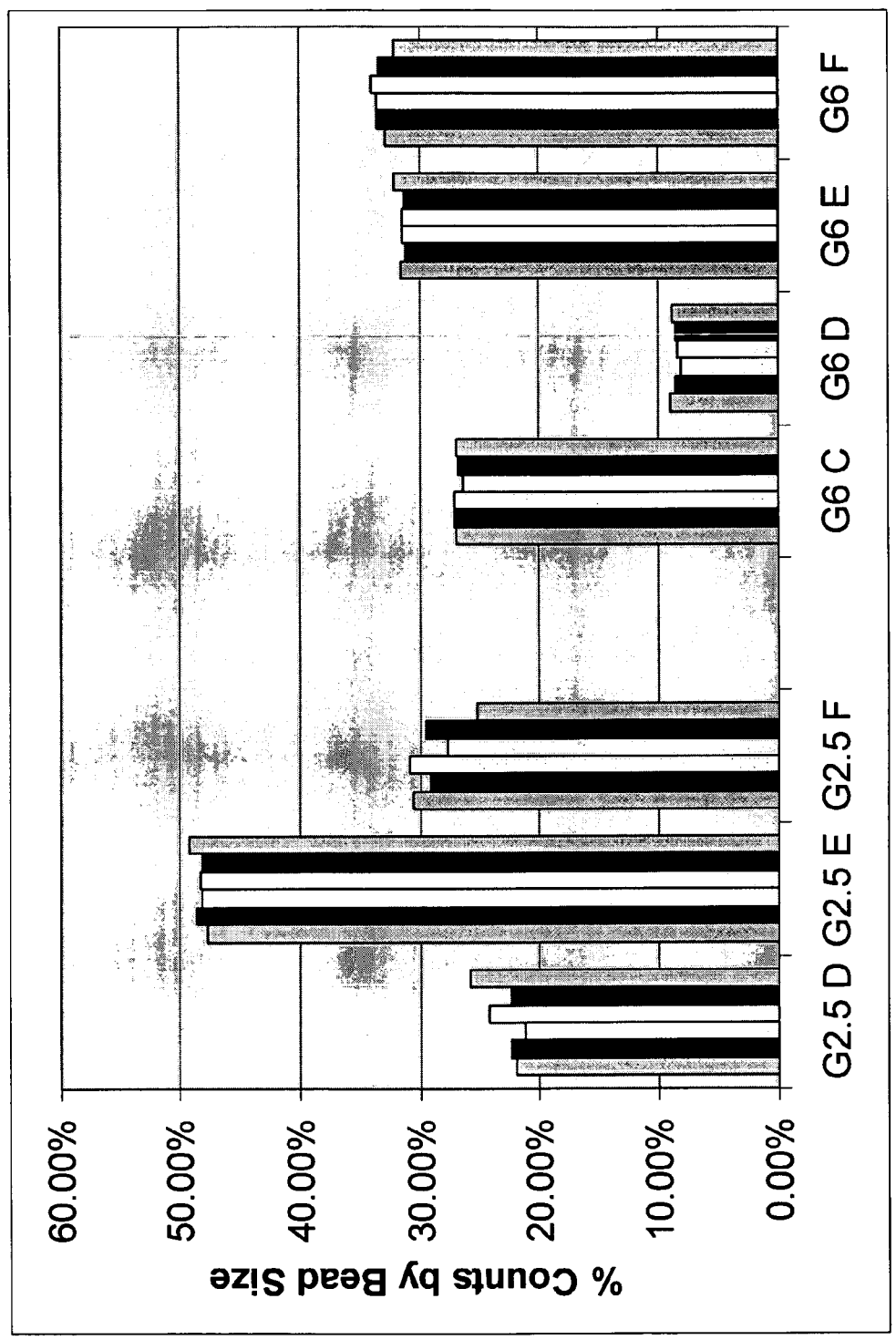
FIG. 7 shows that the signature array measured from a tablet incorporated a population of microparticles into the solid formulation of the tablet matched the expected array.

FIG. 7 shows that the signature arrays measured from the solid formulation containing the population G1 matched that from the controls. Listed in the X-axis are the 7 distinct clusters within the G1 population. For each cluster, the first four bar plots from the left represent the relative counts of entities measured from the tablet containing 5 µl, 10 µl, 15 µL or 25 µl of population G1, respectively, the fifth bar plot from the left represents the mean of the previous four bar plots, and the sixth bar plot from the left represents the relative counts of entities measured from the G1 population directly, i.e., the controls. The relative count is defined as the count of entities per cluster relative to the sum of counts of entities having the same size, i.e., 2.5 µm or 6 µm. Similar results were also observed with the tablets containing the G2, R1, and R2 populations.

This Example demonstrates that a signature array can be associated with an article of product by incorporation into the formulation of a solid product, and such signature can not be dissociated from the product without the product's destruction. Those of ordinary skill in the art of pharmaceutical sciences recognize that association of the signature array with the formulation may be made in other ways using modifications of the method of this Example.

Example 5

Authentication Using Printing Symbols

U.S. Pat. No. 6,071,531 describes a transdermal patch and method for administering 17-deacetyl norgestimate (17-d-Ngm) alone or in combination with an estrogen to prevent ovulation in a woman, as well as compositions and methods for female hormone replacement therapy. The patch comprises a backing layer; and a matrix layer underlying the backing layer comprising a mixture of 17-d-Ngm and a pressure sensitive adhesive. The backing layer is impermeable to the drug and other components of the matrix and defines the top face surface of the patch. It may be made of a single layer or film of polymer, or be a laminate of one or more polymer layers and metal foil.

In the present Example, multiple sets of distinct populations of printable symbols were generated and selected for printing using conventional word processing software and a laser printer in order to simulate a method for printing on the backing layer of the patch, on the packaging of the patch, or both. As shown in Table 5, five conventional characters ("T", "&", "J", "7", and "M") were indexed for printing in one of three indexed different fonts (normal, bold, or italic) and one of three indexed distinguishable styles (normal, strikethrough, or underscore) to create 45 (5×3×3) distinct clusters that can be used to create populations of printed symbols for product authentication.

TABLE 5

Indexing of the 5 conventional characters, the 3 distinguishable fonts, and the 3 identifiable styles

| Character | | Font | | Style | |
|---|---|---|---|---|---|
| Index | Type | Index | Type | Index | Type |
| 1 | T | 1 | Normal | 1 | Normal |
| 2 | & | 2 | Bold | 2 | Strikethrough |
| 3 | J | 3 | Italic | 3 | Underline |
| 4 | 7 | | | | |
| 5 | M | | | | |

Characters of a signature array were selected using an algorithm written in MICROSOFT EXCEL spreadsheet that generated a population of heterogeneous printed symbols as a string, as follows. A look-up table was constructed for the 45 clusters of printed symbols, i.e., all possible combinations of Character×Font×Style, expressed as index position. The corresponding character was incorporated into the look-up table, corresponding to cluster number, as shown in the first two columns of Table 6. A user-specified signature array was designated by randomly selecting particular clusters out of the 45 possible clusters and arbitrarily assigning a frequency of appearance in the specified array for each of the selected cluster. Three representative user-specified signature arrays were designated as shown in Table 6: Array 1, Array 2, and Array 3. For each of 10,000 cells in the spreadsheet, a random number (Random 1) with values between 0 and 1 was generated and multiplied by the number of clusters, then 0.5 was added to the result, and the net result rounded to yield a random cluster number between 1 and 45 (Selected Cluster). Then, a random number with values between 0 and 1 (Random 2) was generated and compared to the fractional frequency specified for the Selected Cluster. If Random 2 was less than said specified frequency, the character corresponding to the Selected Cluster was selected for printing. For example, if Random Number 2 was less than 0.2 in a case where Cluster 3 had been selected randomly from all clusters, "J" was selected for printing, otherwise a value "FALSE" was returned and no character selected; hence, 20% of the time, "J" would be selected when Cluster 3 was the Selected Cluster. If a Selected Cluster had a specified frequency 0, Random Number 2 was never less than 0 and a value "FALSE" was always returned and no character selected. With each recalculation of the spreadsheet, strings of approximately 200+ characters of each array were selected. Representative strings for each of the arrays are as follows:

```
Array 1

MJT MTMMT M&T &MTJTMMMMM && MJJM & MJTMTM & JT && MMMTM

&MJM & JJ &MJ & M && JTMJJ M&JJMJ &MMMMJMMJM&M& MMMM MTJ & J

&& JJ &MMJTM & JJMMT & T MM JJ & JM & JMMM&JJ & TMJJMMJTT && JMT &

JMJMJJMTJ & MTMTJJMTT M&MMJMT MM & JJM & MJ & MMJ &M & JJTJJM &

JMMJJT & MMJ . . .

Array 2

&& MJMTM&&M & MMTJM & MT &&& MJM&TM & TTMTMM J && M MJ &

TMTJTMM & MM MM& JT & TM & MJ & TMTJMTJJJ MMMMM & M && TJMTM

TM & MMJ &&& MJTMM & JTJJJ &MMJ & MTTMTT M&& J &M& TMM &M & J

MMTMJTTM & MJ && TTM & JMTMM &M & MTMJJ & J&M MTMMT M&& M
```

-continued

M<u>T</u>MM &<u>T</u>&*MJ*M*JMJ*M && *J* &*M*<sub>MM</sub><u>T</u> & &*J**M*&<u>T</u>*J*<u>T</u> &<u>T</u> & *MM*<u>TTT</u> & & &   . . .

Array 3

7 *J* 7 *J* J&<u>T</u>7<u>T</u>&<u>77</u>&*T*7*J*<u>MT</u>7 7*JJ* 7 *JTTT*<u>TM</u>T7<u>T</u>77777<u>T7</u>*J* *J*<u>T</u>777&&&7*J*<u>T</u>7&T7&*J*<u>T</u>&<u>T</u>

7777& *JT*7 *T* 77<u>T</u>&<u>TT</u>&<u>M</u>*T*<u>T</u>&*J*<u>T</u>*T*777 *T*<u>T</u>7*T*7*J*& *TT**J*&T7*J* *T*<u>77</u> 7<u>T</u>&&&77&*T*7 *JJ*

&*J**J*7T77 7<u>M</u>&7 *J*7<u>TJ</u>&<u>T</u> 77&&<u>T</u> *T*<u>M</u>*J*<u>T</u>&*T*7 *T*77<u>TT</u>*J*&77 *TT*<u>M</u>*J*<u>T</u>*J*<u>M</u>7777<u>J</u>7 *T*7 *J*

&*J*<u>M</u>*J*<u>M</u>77<u>T</u>77<u>JM</u>77 *J*& *TJ*<u>T</u><u>T</u>77&7 *T*<u>TJ</u>&*T*&7 *T*<u>T</u>7   . . .

The composite result of 25 recalculations of the spreadsheet is shown in Table 6. Close correlation between specified and observed character frequency for each of the three representative signature arrays was observed.

A skilled practitioner recognizes that no sequence repeat is expected in replicate signature arrays generated by the method of this Example. Thus, although it is not a requirement to practice the present invention, articles each labeled

TABLE 6

Arrays of printable symbols

| | | Array 1 | | Array 2 | | Array 3 | |
|---|---|---|---|---|---|---|---|
| Cluster # | Specified Character | Specified Cluster Frequency | Actual Frequency (n = 5434) | Specified Cluster Frequency | Actual Frequency (n = 5599) | Specified Cluster Frequency | Actual Frequency (n = 5443) |
| 1 | T | | 0 | | 0 | | 0 |
| 2 | & | | 0 | | 0 | | 0 |
| 3 | J | 0.2 | 0.208 | 0.1 | 0.104 | | 0 |
| 4 | 7 | | 0 | | 0 | 0.2 | 0.199 |
| 5 | M | 0.1 | 0.098 | 0.2 | 0.198 | | 0 |
| 6 | T | | 0 | | 0 | 0.1 | 0.097 |
| 7 | & | | 0 | | 0 | | 0 |
| 8 | J | | 0 | | 0 | | 0 |
| 9 | 7 | | 0 | | 0 | | 0 |
| 10 | M | | 0 | | 0 | | 0 |
| 11 | *T* | | 0 | | 0 | | 0 |
| 12 | *&* | | 0 | | 0 | | 0 |
| 13 | *J* | 0.1 | 0.096 | 0.1 | 0.104 | | 0 |
| 14 | *7* | | 0 | | 0 | 0.1 | 0.108 |
| 15 | *M* | 0.2 | 0.196 | 0.1 | 0.100 | | 0 |
| 16 | *T̶* | | 0 | | 0 | | 0 |
| 17 | *&* | 0.1 | 0.098 | 0.05 | 0.048 | | 0 |
| 18 | *J̶* | | 0 | | 0 | | 0 |
| 19 | *7̶* | | 0 | | 0 | | 0 |
| 20 | M̶ | | 0 | | 0 | | 0 |
| 21 | T̶ | | 0 | | 0 | | 0 |
| 22 | *&* | 0.1 | 0.098 | 0.2 | 0.199 | | 0 |
| 23 | *J̶* | | 0 | | 0 | 0.1 | 0.099 |
| 24 | *7̶* | | 0 | | 0 | | 0 |
| 25 | M̶ | | 0 | | 0 | | 0 |
| 26 | *T̶* | | 0 | | 0 | 0.1 | 0.096 |
| 27 | &̶ | | 0 | | 0 | | 0 |
| 28 | *J̶* | | 0 | | 0 | | 0 |
| 29 | *7̶* | | 0 | | 0 | | 0 |
| 30 | M̶ | 0.1 | 0.101 | 0.05 | 0.049 | | 0 |
| 31 | <u>T</u> | | 0 | | 0 | 0.05 | 0.049 |
| 32 | <u>&</u> | | 0 | | 0 | 0.05 | 0.052 |
| 33 | <u>J</u> | | 0 | | 0 | 0.05 | 0.052 |
| 34 | <u>7</u> | | 0 | | 0 | | 0 |
| 35 | <u>M</u> | | 0 | | 0 | | 0 |
| 36 | <u>T</u> | 0.1 | 0.105 | 0.2 | 0.199 | | 0 |
| 37 | <u>&</u> | | 0 | | 0 | 0.1 | 0.105 |
| 38 | <u>J</u> | | 0 | | 0 | | 0 |
| 39 | <u>7</u> | | 0 | | 0 | 0.05 | 0.051 |
| 40 | <u>M</u> | | 0 | | 0 | 0.05 | 0.047 |
| 41 | *<u>T</u>* | | 0 | | 0 | 0.05 | 0.044 |
| 42 | *<u>&</u>* | | 0 | | 0 | | 0 |
| 43 | *<u>J</u>* | | 0 | | 0 | | 0 |
| 44 | *<u>7</u>* | | 0 | | 0 | | 0 |
| 45 | *<u>M</u>* | | 0 | | 0 | | 0 | with a signature array constructed as taught in this example will each have a unique sequence, whereas copies of such arrays will have identical sequence, indicating the likelihood of forgery or counterfeiting.

Those of ordinary skill in the art of the present invention recognize that the clusters of printable symbols of the present invention are not limited to the representative characters, fonts, or styles shown in Table 5. For example, symbols like *, ■, ▲, ●, ♣, symbols or Greek alphabet characters or others can replace the Roman alphabet characters used in this example. Whole words or logos may replace or be used with individual characters or symbols in any index position. Color, grayscale level, font size, highlighting or the like can replace or be used with the fonts and styles used in this example. It is apparent that a variety of distinct clusters, by no means limited to the 45 clusters illustrated in Table 5, can be constructed from combinations of the forgoing discretely measurable common properties for the printed symbols.

A skilled practitioner recognizes that printing a code of the present invention is not limited to the backing layer of a transdermal patch. A variety of other suitable surfaces for printing said code can be found on product packages, shrink wrap, containers (such as the vials or prepackaged syringes), on medical devices (such as in the coating of stents or on the casing of implantable defibrillators).

In another embodiment of the present example, distinct microdots are used as Clusters 1-25 and are microprinted on the backing layer of the patch. The microdots have 5 identifiable shapes, and each shape is printed at 5 grayscale levels; grayscale level 1 is black, level 2 is gray (80% black), level 3 is gray (40% black), level 4 is gray (25% black), and level 5 is unfilled. The identity of Clusters 1-25 is shown in detail in Table 8.

TABLE 7

25 clusters of microdots having 5 identifiable shapes and printed at 5 distinguishable grayscale levels

| Cluster ID # | Symbol | Grayscale |
|---|---|---|
| 1 | ✱ | 1 |
| 2 | ✱ | 2 |
| 3 | ✱ | 3 |
| 4 | ✱ | 4 |
| 5 | ✱ | 5 |
| 6 | ● | 1 |
| 7 | ● | 2 |
| 8 | ● | 3 |
| 9 | ● | 4 |
| 10 | ● | 5 |
| 11 | ■ | 1 |
| 12 | ■ | 2 |
| 13 | ■ | 3 |
| 14 | ■ | 4 |
| 15 | ■ | 5 |
| 16 | ▲ | 1 |
| 17 | ▲ | 2 |
| 18 | ▲ | 3 |
| 19 | ▲ | 4 |
| 20 | ▲ | 5 |
| 21 | ♦ | 1 |
| 22 | ♦ | 2 |
| 23 | ♦ | 3 |
| 24 | ♦ | 4 |
| 25 | ♦ | 5 |

A population of heterogeneous microdots is printed on the backing layer of the patch uniformly across its surface and in such a manner that dots do not overlap. A total of 10 to 10,000 dots are printed per area of the patch to be analyzed by low-power microscopy. Table 8 shows exemplary signature arrays and compositions of the populations of heterogeneous microdots corresponding to three product authentication codes for 3 lots of product (Lot A, Lot B, and Lot C) constructed from only Clusters 1-25. In this example, signature arrays corresponding to Lot B and Lot C comprise dots from identical clusters, however said arrays are readily distinguishable on the basis of counts/cluster in the arrays. This example also shows that Cluster 1, for example, is printed at the same ratio to all three populations of dots to be used as an internal reference.

TABLE 8

Exemplary signature arrays and compositions of the populations of heterogeneous microdots corresponding to three product authentication codes

| Cluster ID # | Sig. Array 1 (Lot A.) 1(1), 8(5), 12(2), 13(2), 21(1), 22(3) | Sig. Array 2 (Lot B.) 1(1), 2(1), 3(1), 4(4), 6(1), 7(1), 8(1), 10(3), 11(2), 13(5), 14(4), 15(5), 18(4), 20(3), 24(1), 25(1) | Sig. Array 3 (Lot C.) 1(1), 2(5), 3(5), 4(4), 6(3), 7(5), 8(5), 10(3), 11(2), 13(5), 14(4), 15(5), 18(4), 20(3), 24(4), 25(5) |
|---|---|---|---|
| 1 | 1 per 14 dots | 1 per 38 dots | 1 per 62 dots |
| 2 | — | 1 per 38 dots | 5 per 62 dots |
| 3 | — | 1 per 38 dots | 5 per 62 dots |
| 4 | — | 4 per 38 dots | 4 per 62 dots |
| 5 | — | — | — |
| 6 | — | 1 per 38 dots | 3 per 62 dots |
| 7 | — | 1 per 38 dots | 5 per 62 dots |
| 8 | 5 per 14 dots | 1 per 38 dots | 5 per 62 dots |
| 9 | — | — | — |
| 10 | — | 3 per 38 dots | 3 per 62 dots |
| 11 | — | 2 per 38 dots | 2 per 62 dots |
| 12 | 2 per 14 dots | — | — |
| 13 | 2 per 14 dots | 5 per 38 dots | 5 per 62 dots |
| 14 | — | 4 per 38 dots | 4 per 62 dots |
| 15 | — | 5 per 38 dots | 5 per 62 dots |
| 16 | — | — | — |
| 17 | — | — | — |
| 18 | — | 4 per 38 dots | 4 per 62 dots |
| 19 | — | — | — |
| 20 | — | 3 per 38 dots | 3 per 62 dots |
| 21 | 1 per 14 dots | — | — |
| 22 | 3 per 14 dots | — | — |
| 23 | — | — | — |
| 24 | — | 1 per 38 dots | 4 per 62 dots |
| 25 | — | 1 per 38 dots | 5 per 62 dots |

Analysis of the compositions or cluster membership of the population of heterogeneous microdots associated with a product is determined using a microscope, or preferably an automated microscope, and visual identification of shape and grayscale, or preferably, automated image analysis using Image-Pro Plus Software with Scope-Pro plug-in (both from MediaCybernetics, Sylver Spring, Md.). The signature array of the population of heterogeneous microdots can then be deduced.

Those of ordinary skill in the art can use microdots with alternative construction. For example, the microdot's color or size may replace grayscale.

A skilled practitioner recognizes that printing a code of the present invention is not limited to the backing layer of a transdermal patch. A variety of other suitable surfaces for printing said code can be found on product packages, containers (such as the vials or prepackaged syringes), on medical devices (such as in the coating of stents or on the casing of implantable defibrillators).

Example 6

Product Made by the Process of Incorporating a Signature Array

This Example illustrates a process for making a product using attributes of the signature array of the present invention for quality control and release testing, while maintaining all of the benefits that said array has for authenticating the product. Particularly, this Example demonstrates a process that would be useful for manufacturing a liquid product like PROCRIT.

For the purpose of illustration, it is assumed that the last step of the PROCRIT manufacturing process is to combine two separate mixtures that are added in a 9:1 ratio to yield the final product, and that said last step has an acceptance range of +/−10% versus the target. For the portion intended to be present in 9 parts, a mixture designated Portion A was formulated comprising all of the components of PROCRIT except the active ingredient erythropoietin alpha. For the second mixture component, designated Portion B, Dulbecco's phosphate buffered saline+0.1% Triton-X100 was used as a surrogate for the active ingredient erythropoietin alpha at 10× the concentration of the final product.

Populations of fluorescent microparticles from Invitrogen Corporation as described above in Example 1 were prepared by mixing the designated quantities of each cluster of microparticles as described in Table 9. Sub-population Y was added to Portion B at approximately 10× the dilution (i.e., 250 μl of Sub-population Y per 1 ml Portion B) that Sub-population X was added to Portion A (i.e., 25 μl of Sub-population X per 1 ml Portion A), such that when 3 replicates were made of 9 parts labeled Portion A plus 1 part labeled Portion B, a target ratio of total counts obtained for all clusters in Sub-population Y to the corresponding total counts obtained from Sub-population X was empirically determined to be 0.837.

TABLE 9

Populations of Invitrogen microparticles for product quality control and release testing

| Sub-Population X | (μl) | Sub-Population Y | (μl) |
|---|---|---|---|
| Green 2.5 μ suspension D | 100 | Deep Red 2.5 μ suspension D | 200 |
| E | 200 | E | 100 |
| F | 100 | F | 200 |
| Green 6 μ suspension C | 200 | Deep Red 6 μ suspension C | 100 |
| D | 100 | D | 200 |
| E | 200 | E | 100 |
| F | 200 | F | 200 |
| Total Volume | 1100 | Total Volume | 1100 |

To simulate both the proper manufacturing process and potential manufacturing errors, a constant volume of Portion A was mixed with varying amounts of Portion B according to the ratios listed Table 10. Thus, in addition to the correct 9:1 ratio, three cases were simulated wherein the addition of the active ingredient erythropoietin alpha was incorrectly low (Trials 2, 3 and 4) and three cases were simulated wherein said addition was incorrectly high (Trials 6, 7, and 8). Also included is a simulation of inadvertent failure to add any erythropoietin alpha (Trials 1).

TABLE 10

Simulation of the manufacturing process

| Trial # | Portion A | Portion B |
|---|---|---|
| 1 | 9 parts | None |
| 2 | 9 parts | 0.5 parts |
| 3 | 9 parts | 0.75 parts |
| 4 | 9 parts | 0.875 parts |
| 5 | 9 parts | 1 part |
| 6 | 9 parts | 1.125 parts |
| 7 | 9 parts | 1.25 parts |
| 8 | 9 parts | 1.5 parts |

Figure 8:
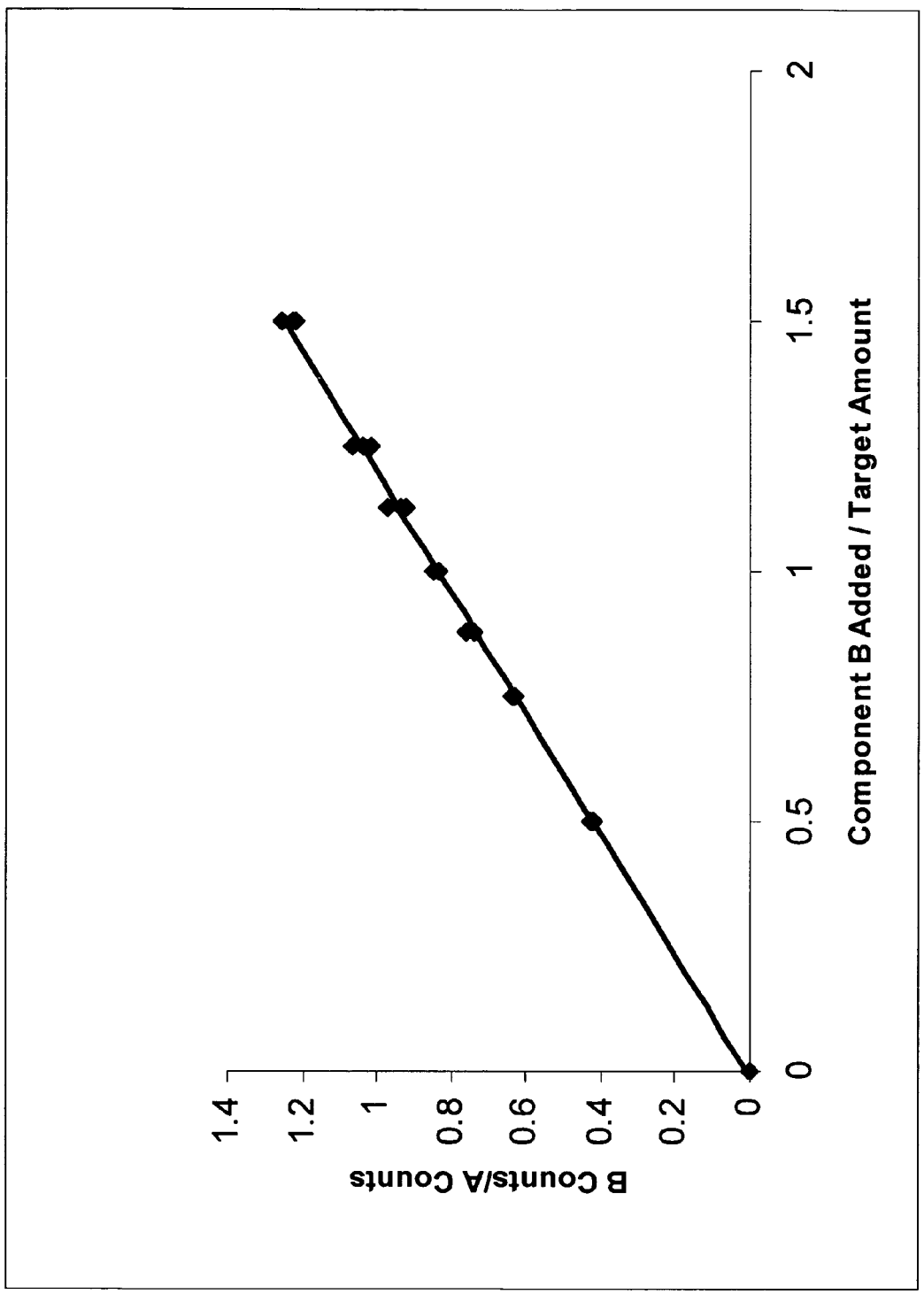
FIG. 8 shows the linear regression analysis of the target and measured count ratios when a signature array was used to control and release a manufacturing process wherein $y=0.826x+0.0096$, $R^2=0.9983$.

To simulate quality control and release testing of the Portion A/Portion B mixing step, triplicate samples were thoroughly vortexed and analyzed by FACS. As mentioned above, the target ratio of total counts obtained for all clusters in Sub-population Y to the corresponding total counts obtained from Sub-population X was expected to be 0.837. FIG. 8 shows the ratio of total counts obtained for all clusters in Sub-population Y/Portion B to the corresponding total obtained from Sub-population X/Portion A as a function of the fraction Portion B added/target amount Portion B. The target count ratio of linear regression analysis showed excellent correlation between measured and expected values. FIG. 8 also shows the mixtures of Trials 4 and 6 to be outside of the acceptance range of +/−10% versus the target Those of ordinary skill in the art of pharmaceutical sciences recognize that a similar method as that described in this Example may be employed for quality control and release testing of mixtures used to make solid formulations. Additionally, it is evident to the skilled practitioner that this Example allows for the methods of this invention to substitute for other costly and or more complicated analytical methods that might otherwise be used to assure proper mixing of formulation components.

The skilled artisan recognizes that the signature array of this invention may be validated to replace costly analytical methods in product release of pharmaceutical products or virtually any manufactured product. The skilled artisan also recognizes that products so released maintain all the advantages of the present invention in conferring ready authentication to said products.

Example 7

Tampering by Dilution and Counterfeit Product Revealed Using Fluorescent Microparticles In the present example, dilution of a labeled liquid product was detected by measuring a change in the count of microparticles per unit volume of a liquid product. This Example 7 illustrates that the present invention is useful to detect tampering of such a product by dilution or counterfeiting of a product using a dilution of genuine product.

A. Spike and Recovery:

The Luminex 100 (Luminex Corporation, Austin, Tex.) directly measures microparticle counts per unit volume of samples, and hence has the capability to detect microparticle counts per cluster of a population per unit volume of a product. A "Spike and Recovery" experiment was conducted to assure that, the number of microbeads detected per unit volume of labeled product using the Luminex 100 instrument was proportionate to the number of microparticles added to the product for product authentication purpose detected by hemacytometer counting of the microparticles.

Microparticles were from Luminex Corporation (Austin, Tex.) labeled with a red fluorescent dye (Dye 1, as defined above) and a near-infrared (NIR) fluorescent dye (Dye 2 as defined above). Different final concentrations of each of the red and NIR fluorescent dyes were used to label the microparticles in 20 distinct combinations. Microparticles from each such combination were distinguishable from microparticles from each other combinations on the Luminex 100 instrument, with the Luminex Data Collector software, version 1.7. Therefore, the microparticles labeled with the 2 dyes at various concentrations can be classified into 20 clusters as shown in Table 11. More clusters are possible by increasing the number of choices of the possible final concentrations of one or both of the dyes. For example, 50 clusters are possible when the microparticles are labeled with the combination of red dye at one of 10 final concentrations and NTR dye at one of 5 final concentrations. In addition, more clusters can be obtained by using one or more additional dyes. For example, microparticles labeled with the combination of the red dye at one of 5 final concentrations and NTR at one of 5 final concentrations can be assigned into 25 distinct clusters. By introducing a third dye, a yellow dye, at only one concentration, at least 35 additional distinct clusters can be obtained: 25 of which comprise microparticles labeled with all three dyes, 5 of which comprise microparticles labeled with the red and yellow dyes, and 5 of which comprise microparticles labeled with the NTR and yellow dyes.

TABLE 11

Twenty clusters of microparticles labeled with two dyes at different final concentrations.

| Group 1 | Group 2 | Group 3 | Group 4 |
|---------|---------|---------|---------|
| 24 | 55 | 21 | 48 |
| 73 | 22 | 77 | 51 |
| 6 | 52 | 16 | 36 |
| 59 | 34 | 4 | 2 |
| 10 | 46 | 43 | 32 |

To facilitate the hemacytometer counting of the microparticles within each of the 20 clusters, microparticles were divided into 4 groups and each of which comprises 5 distinct clusters, as listed in listed in Table 11. Microspheres from each of the twenty clusters shown in Table 11 were diluted to a concentration of approximately 400,000 microsphere/mL with 1 mL of PROCRIT® (EPOETIN ALFA 40, lot P004839) based upon an initial estimate from the products' label concentration ($1.25 \times 10^7$ microspheres/mL). The actual microsphere concentration added was determined by introducing 10 μL the labeled PROCRIT that had been diluted 1/10 with Phosphate Buffer Saline (PBS) pH 7.4 onto a hemacytometer. The actual microsphere counts from a hemacytometer were used subsequently to calculate the expected count recovery from labeled PROCRIT.

To make a determination on the Luminex 100, the microsphere sets were combined into the four groups listed in Table 1 before centrifugation. Sample preparations were done in triplicates and stored at room temperature. Thirty-two (32) μL from each microsphere set were placed in a USA Scientific microcentrifuge tube and concentrated by centrifigation for 2 minutes at 14,000 rpm. The supernatant was removed and the microspheres were suspended in 1 mL of PROCRIT at a resulting concentration of each microsphere set was 400,000 microspheres/mL as determined above.

Separately, in order to measure actual recovery upon analysis on the Luminex 100, one hundred (100) μL of each microsphere group were diluted into 900 μL of PBS pH 7.4. This 1/10 dilution of microsphere formulation produced a working microsphere mixture that was within the Luminex 100 instrument analysis range. Seventy (70) μL of each working microsphere mix were transferred to a sample well (8 replicates for each microsphere mix) and 50 μL were analyzed using a Luminex 100 instrument.

The results showed that for each of the 20 clusters, the percent recovery (individual cluster count) measured using a Luminex 100 matched the corresponding cluster counts measured from a hemacytometer.

B. "Tampering" Analysis

A "Tampering" experiment was conducted to detect tampering by dilution or counterfeiting of a product using a dilution of genuine product via observing a change in counts per unit volume of the product of microparticles that are incorporated into the product for product authentication.

The tampering analysis experiment was done using two serial dilutions of the marked PROCRIT that had been labeled with a population of microparticles comprising the 20 clusters described in Example 7, section A. Two dilution series in PBS pH 7.4 were performed in parallel as follows. The first dilution series consisted of a 1/10, 1/100, and 1/1000 serial dilution of the marked PROCRIT, while the second series consisted of 1/2, 1/4, 1/8, and 1/16 dilution of the marked PROCRIT. For each point in each series, 100 μL was added to 900 μL of PBS pH 7.4 to produce a working sample for analysis on the Luminex 100. Seventy-five μL of working sample was transferred to a sample well (8 replicates for each microsphere mix) and 50 μL were analyzed using a Luminex 100 instrument.

Figure 9:
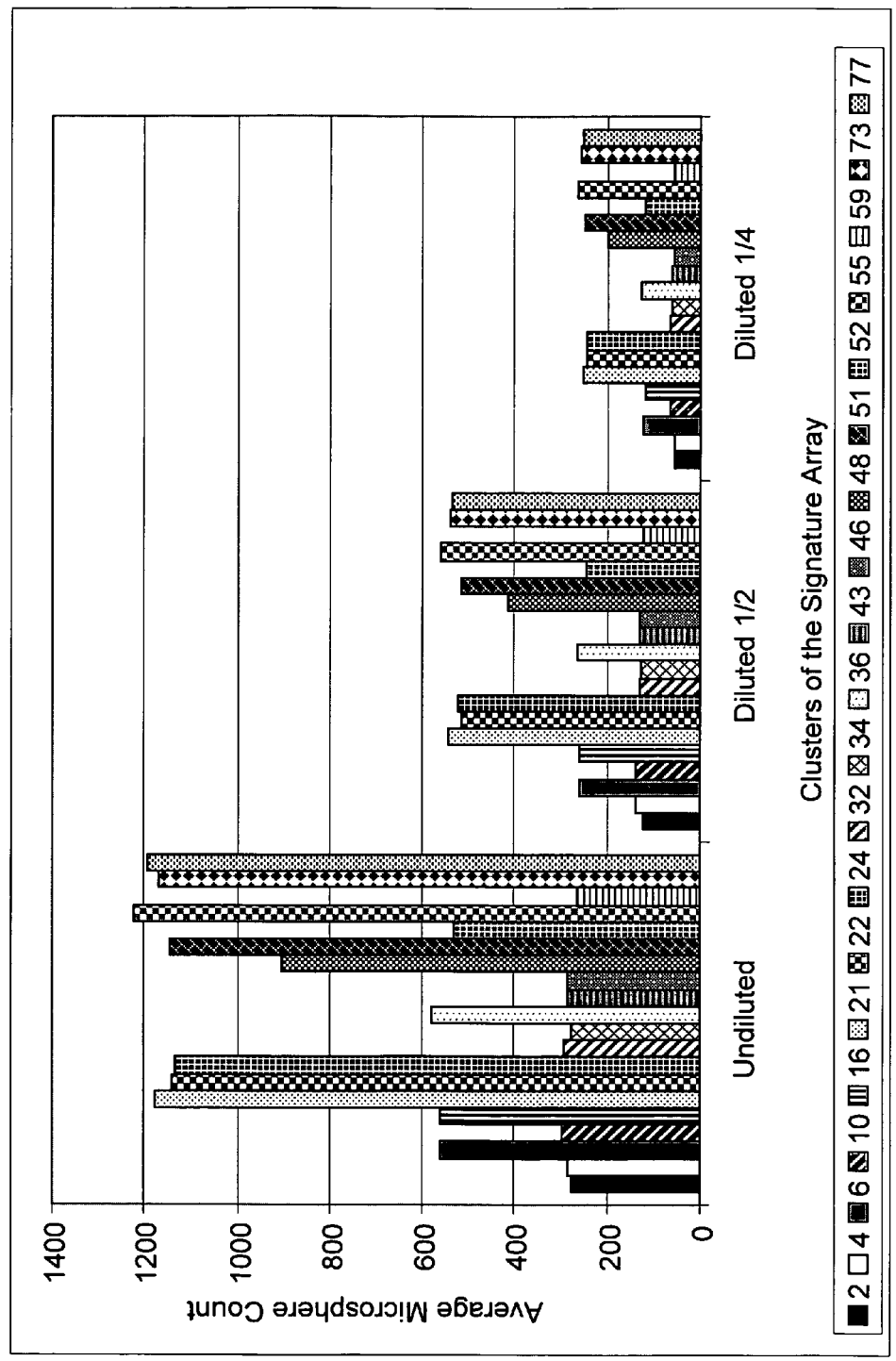
FIG. 9 is a plot of the average count (from the 8 replicates) of microparticles of each of the 20 clusters at different dilutions of PROCRIT, which had been marked with the 20 clusters.

FIG. 9 is a plot of the average count (from the 8 replicates) of microparticles of each of the 20 clusters at different dilutions of the PROCRIT, which had been marked with the 20 clusters. As shown in FIG. 9, although the relative frequency of each cluster remained constant (i.e., the cluster composition is unchanged), the count of microparticles of each cluster per unit volume analyzed, and hence total counts, decreased as a function of dilution of product 1:2 and 1:4. Observed counts continued to decrease as a function of dilutions of 1:8, 1:10, 1:16, and 1:100. These results indicate that the present invention is useful to detect tampering of such a product by dilution or counterfeiting of a product by diluting a genuine product.

Those of ordinary skill recognize that a similar method as that described in this Example may be employed to detect tampering of any formulated product, whether liquid or solid, by dilution or counterfeiting of such a product using a dilution or "cutting" of a genuine product. The skilled artisan also recognizes that said products maintain all the advantages of the present invention in conferring ready authentication to said products.

Example 8

Authentication Using Dissolving Microparticles

U.S. Pat. No. 6,586,012 describes an orally consumable liquid composition comprising a pharmaceutically active agent in particle form contained in a liquid suspension having a pH greater than about 6.0, each particle comprising a core of pharmaceutically active agent, optionally associated with inactive pharmaceutical adjuvants; the core being coated with a taste masking effective amount of a polymer blend of (a) dimethylaminoethyl methacrylate and neutral methacrylic acid ester (MM/MAE) and (b) a cellulose ester, in an aqueous vehicle, wherein the polymer blend has a weight ratio of the cellulose ester to the MM/MAE of about 40:60 to about 90:10. The liquid composition utilizes a "reverse enteric coating" which is soluble in the acidic pH of the stomach, generally about 1.0 to 4.0, but relatively insoluble at the non-acidic pH of the mouth. The coatings provide for rapid release and absorption of the drug, which is generally desirable in the case of liquid dosage forms. In particular, U.S. Pat. No. 6,586,012 gives as an example preparation of taste masked levofloxacin composition for oral liquid administration.

In the present example, levofloxacin particles are prepared by admixing dyes with other components, for example as described in U.S. Pat. No. 6,586,012, otherwise used to form a liquid composition for oral administration suitable for pediatric therapy. Acceptable dyes include, but are not limited to, fluorescein dyes, including carboxyflourescein, rhodamine dyes, including sulforhodamine B, food coloring dyes, and the like. Combinations of dyes are chosen to be compatible with the analytical method to be used in revealing the signature array of the levofloxacin particles.

Similar to Example 7, different clusters of levofloxacin particles are obtained by labeling the particles with one or more dyes at one or more final concentrations. Also similar to Example 7, populations of heterogeneous levofloxacin particles with different signature arrays can be obtained by mixing separate portions of levofloxacin particles from appropriate clusters. The representative signature arrays and compositions of the population of levofloxacin particles of Table 12 can be replicated to represent product authentication codes for 3 lots of product, Lot A, Lot B, and Lot C, except that in this Example unmarked levofloxacin particles would substitute for the parts of buffer used in Example 7.

The populations of levofloxacin particles labeled with appropriate fluorescent dyes are analyzed on the Becton Dickinson FACScan flow cytometer for elucidation of their corresponding signature arrays. The fluorescence properties of each of the distinct populations of levofloxacin particles used as Clusters 1-25 are measured individually by analysis of a suspension in basic buffer to yield approximately $10^5$ event counts to be used to define each cluster's location in fluorescence data space. For analysis, Levofloxacin lots are suspended uniformly in buffer at basic pH, then a dilution of approximately 100 microliters is analyzed to measure about $10^2$ event counts, or preferably $10^3$ event counts, corresponding to levofloxacin particles of Cluster 1. From the data obtained from each lot, the ratio of event counts corresponding to Clusters 2-25 are calculated according to the methods described in more detail in Example 7.

Alternatively, the signature array is determined using microscopy, or more preferably, an automated microscope method.

It is evident to the skilled practitioner that the methods of this example do not result in ingestion of any labeling particles in the course of using products so labeled in human therapy, in that the particles dissolve. Further, careful choice of dyes will result in consumption of only trace amounts of dye, and in some cases, of dye that is otherwise deemed safe for human consumption.

The methods of this Example are not limited to taste masked formulations intended for liquid oral administration. U.S. Pat. No. 6,696,091 describes a solid dosage formulation of topiramate, an anticonvulsant, in a sprinkle formulation comprising core particles of the active agent which is taste-masked with a second layer to obscure the taste of topiramate.

The core particles can comprise topiramate alone, or with one or more excipients which are then formed into granules or beads, the preferred solid dosage formulation of which is microspheres which may be sprinkled onto soft food (e.g., baby food) and swallowed by the patient along with the food. Those of ordinary skill in the art of pharmaceutical sciences may be employed to prepare such microspheres comprising the active agent of topiramate along with the dyes needed to practice the invention as described in this Example.

Example 9

Combining the Signature Array Code with Radio Frequency Identification (RFID) to Increase Product Security A product authentication code based on a signature array of a population of entities can be combined with other product authentication means for product authentication. This Example illustrates the combination of a product authentication code encoded by a population of heterogeneous microdots with RFID for authentication of PROCRIT, erythropoietin-alpha for treating anemia, supplied in lyophilized form for reconstitution and injection. As a valuable pharmaceutical product, PROCRIT has been widely counterfeited, which has resulted in patients in need of therapy having been denied the authentic product's beneficial effects.

Three lots of PROCRIT, designated Lot A, Lot B and Lot C, are packaged with RFID microchips. The three lots are also labeled with the signature array codes shown in Table 15, constructed from Clusters 1-25 listed in Table 7. Each of the signature array codes matches specifically to a RFID microchip. A population of heterogeneous microdots is printed on the stoppers to be used in each lot (as described in further detail in Example 5), such populations corresponding to three product authentication codes for 3 lots of product (Lot A, Lot B, and Lot C).

TABLE 15

Signature array product authentication codes associated with products that have been labeled with RFID microchips

| Sig. Array 1 (Lot A. RFID1) | Sig. Array 2 (Lot B. RFID2) | Sig. Array 3 (Lot C. RFID3) |
|---|---|---|
| 1(1), 8(5), 12(2), 13(2), 21(1), 22(3) | 1(1), 2(1), 3(1), 4(4), 6(1), 7(1), 8(1), 10(3), 11(2), 13(5), 14(4), 15(5), 18(4), 20(3), 24(1), 25(1) | 1(1), 2(5), 3(5), 4(4), 6(3), 7(5), 8(5), 10(3), 11(2), 13(5), 14(4), 15(5), 18(4), 20(3), 24(4), 25(5) |

To authenticate Lots A-C in the supply chain, the signature array codes carried by the RFID microchips are read by appropriate scanning devices, and such code information is automatically transferred to the PC controlling the automated image analysis device. PROCRIT vial stoppers are scanned and signature array codes revealed. Table 16 shows the decision matrix, demonstrating the enhanced product protection conferred by the present inventions' use in combination with known product authentication technology, like RFID.

TABLE 16

Authentication by combining RFID with Signature Array Code

| Valid RFID code detected | Valid Signature array code detected | RFID & Signature Array codes match | Conclusion |
|---|---|---|---|
| Yes | Yes | Yes | Authentic Product |
| Yes | Yes | No | Evidence of tampering |
| Yes | No | n/a | Evidence of tampering |
| No | Yes | n/a | Evidence of tampering |

Those of ordinary skill in the art can use microdots with alternative construction, or other entities, such as microparticles (embedded or affixed in a suitable binding matrix) to label the stoppers in this example. Additionally, the skilled artisan recognizes that other components of the packaging are suitable for labeling with the signature array or that RFID or other known product authentication technology may be used in conjunction with a liquid suspension and particulate arrays like the ones described in the above Examples.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references are hereby incorporated into this application in their entirety.

What is claimed is:

1. A method of marking a product for product authentication, comprising the steps of:
   a) associating a population of entities with the product, wherein the population comprises at least two distinct clusters of entities having detectable counts or relative counts of entities per cluster; and
   b) assigning a signature array of the population of entities to the product as a product authentication code, wherein the signature array comprises information about the counts or relative counts of entities of at least two distinct clusters of entities within the population.

2. The method of claim 1 further comprising a step of correlating the count or relative count of entities of one or more clusters that form the population of entities with a specific piece of information about the product.

3. The method of claim 2 wherein the specific piece of information about the product is selected from the amount, concentration, or presence or absence of a product component.

4. The method of claim 1, wherein each of the at least two distinct clusters of entities has one or more discretely measurable common properties that are shared by entities within said cluster, but not by entities within any other cluster.

5. The method of claim 4, wherein the one or more discretely measurable common properties are properties of one or more tags associated with the entities.

6. The method of claim 5, wherein the one or more tags associated with the entities is selected from the group consisting of: colors, fluorescent dyes, ultraviolet radiation dyes, luminescent compositions, printed symbols, microparticles, haptens, nucleotides, polypeptides, scents, and a combination thereof.

7. The method of claim 4, wherein the one or more discretely measurable properties of the entities are the size of the entities, the style of the entities, or the shape of the entities.

8. The method of claim 1, wherein the population of entities comprises microparticles.

9. The method of claim 8, wherein the microparticles are labeled with at least two discretely measurable fluorescent dyes.

10. The method of claim 9, wherein the at least two discretely measurable fluorescent dyes are present on the same microparticle.

11. The method of claim 8, wherein the microparticles are labeled with a fluorescent dye in at least two detectable different intensity levels.

12. The method of claim 1, wherein the population of entities comprises printed symbols.

13. The method of claim 1, wherein the population of entities comprises one or more types of entities selected from the group consisting of microparticles, printed symbols, nucleic acid molecules, peptides, polypeptides, hapten, or a combination thereof.

14. The method of claim 1, wherein during the step of associating a population of entities with the product, the population is associated with the product by incorporation into the composition of the product.

15. The method of claim 1, wherein during the step of associating a population of entities with the product, the population is associated with the product by incorporation on or near the surface of the product.

16. The method of claim 1, wherein during the step of associating a population of entities with the product, the population is associated with the product by being present in the product container, packaging, labeling, other medium that is associated with the product, or a combination thereof.

17. The method of claim 1, wherein the product is a pharmaceutical product.

18. The method of claim 17, wherein the pharmaceutical product is a liquid pharmaceutical product.

19. The method of claim 17, wherein the product is a solid pharmaceutical product.

20. The method of claim 1, wherein the entities are non-toxic in amounts used.

21. A coded product comprising a product and a product authentication code wherein the product authentication code is encoded by a signature array of a population of entities associated with the product, wherein the signature array comprises information about the counts or relative counts of entities of at least two distinct clusters of entities within the population.

22. The product of claim 21 being a pharmaceutical product.

23. The product of claim 22 being a solid pharmaceutical product.

24. The product of claim 22 being a semi-solid pharmaceutical product.

25. The product of claim 22 being a liquid pharmaceutical product.

26. The product of claim 22 being an injectable pharmaceutical product.

27. The product of claim 21 being selected from the group consisting of recordings, textiles, leather goods, and automotive components.

28. The product of claim 21 further comprising an additional product authentication means.

29. The product of claim 28 wherein the additional product authentication means uses a radio frequency identification (RFID) tag, a spectroscopic ink, a hologram, a reflective paper, a laser etched paper, or a bar code.

30. The product of claim 28 wherein the additional product authentication means uses a radio frequency identification tag.

31. An improvement to a product, wherein the improvement is a product authentication code that is encoded by a signature array of a population of entities associated with the product, wherein the signature array comprises information about the counts or relative counts of entities of at least two distinct clusters of entities within the population.

* * * * *